(12) United States Patent
Kloek et al.

(10) Patent No.: US 6,818,433 B1
(45) Date of Patent: Nov. 16, 2004

(54) NEMATODE PGM-LIKE SEQUENCES

(75) Inventors: Andrew P. Kloek, St. Louis, MO (US); Deryck Jeremy Williams, St. Louis, MO (US); Brandy Salmon, Durham, NC (US); John D. Bradley, St. Louis, MO (US)

(73) Assignee: Divergence, Inc., St. Louis, MO (US)

( * ) Notice: Subject to any disclaimer, the term of this patent is extended or adjusted under 35 U.S.C. 154(b) by 0 days.

(21) Appl. No.: 10/082,894

(22) Filed: Feb. 26, 2002

Related U.S. Application Data

(60) Provisional application No. 60/271,781, filed on Feb. 27, 2001.

(51) Int. Cl.[7] .......................... C12N 9/12; C12N 15/00; C12N 1/20; C12N 9/00; C07H 21/04
(52) U.S. Cl. ................................ 435/252.3; 435/320.1; 435/233; 435/254.11; 435/325; 435/419; 536/23.2
(58) Field of Search ............................. 435/194, 320.1, 435/252.3, 254.11, 325, 419; 536/23.2

(56) References Cited

PUBLICATIONS

GenBank Accession No. AW152739, Allen et al., Aug. 28, 2000.
GenBank Accession No. AW499468, Fischer et al., Mar. 1, 2000.
GenBank Accession No. AW783013, McCarter et al., May 10, 2001.
GenBank Accession No. BF423140, Blaxter et al., Nov. 28, 2000.
GenBank Accession No. NM_059495, Genome Sequencing Consortium, Dec. 3, 2001.
Butterworth et al., "The Effects of Specific Metabolic Inhibitors on the Energy Metabolism of *Globodera*.." Revue Nematol. 21(1):63–67, 1989.
Chevalier et al., "*Trypanosoma brucei* Contains a 2,3-bisphosphoglycerate Independent Phosphoglycerate Mutase" Eur. J. Biochem. 267:1464–1472, 2000.
Fothergill–Gilmore et al., "The Phosphoglycerate Mutases" Adv. Enzymology 62:227–313, 1989.
Forthergill–Gilmore et al., "Evolution of Glycolysis" Prog. Biophys. Mol. Biol. 59:105–235, 1993.
Fraser et al., "The Two Analogous Phosphoglycerate Mutases of *Escherichia coli*" FEBS Lett. 455:344–348, 1999.
Galperin et al., "A Superfamily of Metalloenzymes Unifies Phosphopentomutase and Cofactor–Independent.." Protein Science 7:1829–1835, 1998.
Martin, R.J., "Modes of Action of Anthelmintic Drugs" The Vet. J. 154:11–34, 1997.
Rigden et al., "The 2.3 Å X–ray Crystal Structure of *S. cerevisiae* Phosphoglycerate Mutase" J. Mol. Biol. 276:449–459, 1998.
Schulman et al., "Purification, Characterization and Inhibition by MK–401 of *Fasciola Hepatica* Phosphoglyceratemutase" Mo. And Bioch. Parasitology 5:321–332, 1982.

Primary Examiner—Rebecca L. Prouty
Assistant Examiner—Malgorzata Walicka
(74) Attorney, Agent, or Firm—Fish & Richardson P.C.

(57) ABSTRACT

Disclosed is a nucleic acid molecule from nematodes encoding for phosphoglycerate mutase (PGM) polypeptides. The PGM-like polypeptide sequence is also provided, as are vectors, host cells, and recombinant methods for production of PGM-like nucleotides and polypeptides. The invention further relates to screening methods for identifying inhibitors and/or activators, as well as methods for antibody production. Such inhibitors are useful for control nematode infection.

10 Claims, 5 Drawing Sheets

```
1
gtt taa tta ccc aag ttt gag ATG GAC AAA TAT CAA AAT GTT CAA CAA AAA GTC TGT CTT
                                M   D   K   Y   Q   N   V   Q   Q   K   V   C   L
61
GTA GTT ATT GAT GGA TGG GGC CTT TCC GAT GAA CAA CAC GGG AAT GCA ATT GCT AAA GCT
V   V   I   D   G   W   G   L   S   D   E   Q   H   G   N   A   I   A   K   A
121
AAA ACG CCT ATT ATG GAC AAA CTT TGT TCT GGA AAT TGG CAA AAA TTG GAA GCA CAC GGT
K   T   P   I   M   D   K   L   C   S   G   N   W   Q   K   L   E   A   H   G
181
CTT CAT GTT GGA TTG CCA GAA GGC TTA ATG GGA AAT TCT GAA GTT GGA CAT TTG AAT ATA
L   H   V   G   L   P   E   G   L   M   G   N   S   E   V   G   H   L   N   I
241
GGA GCT GGA AGA GTT ATT TAT CAA GAT ATT GTT CGA ATT AAT TTG GCT GTT CAA CGA AAC
G   A   G   R   V   I   Y   Q   D   I   V   R   I   N   L   A   V   Q   R   N
301
GAG TTT GTT ACA AAT CCT CAG ATT GTT GCA TCA GCT GAG CGT GCA AAG AAG GGG AGT GGT
E   F   V   T   N   P   Q   I   V   A   S   A   E   R   A   K   K   G   S   G
361
CGA TTG CAT TTA TTA GGA CTG GTT AGC GAT GGT GGT GTC CAC TCT CAT ATT GAT CAT CTT
R   L   H   L   L   G   L   V   S   D   G   G   V   H   S   H   I   D   H   L
421
TTT GCG TTG ATA CGT GCA TTT AAA CAA TTA CAA GTG CCA AAG GTT TTC ATT CAC TTT TTT
F   A   L   I   R   A   F   K   Q   L   Q   V   P   K   V   F   I   H   F   F
481
GCT GAT GGT CGA GAT ACT TCG CCA ACA AGT GGA GCT GGT TAT CTT GAA CAA CTT CTT CAA
A   D   G   R   D   T   S   P   T   S   G   A   G   Y   L   E   Q   L   L   Q
541
TTT ATT GCT TCG GAA AAG TAC GGA GAA TTG GCT ACT ATT ACT GGA CGT TAT TAT GCA ATG
F   I   A   S   E   K   Y   G   E   L   A   T   I   T   G   R   Y   Y   A   M
601
GAT AGG GAC AAA AGA TGG GAG CGT ATT AAG ATG GCT TAT GAG GCA ATT GTT GGA GGT ATT
D   R   D   K   R   W   E   R   I   K   M   A   Y   E   A   I   V   G   G   I
661
GGA CAA AAA GCC ACC GTT GAT AAG GCT GTC GAT GTT GTT AGA GAG CGA TAT GCT CAA TCT
G   Q   K   A   T   V   D   K   A   V   D   V   V   R   E   R   Y   A   Q   S
721
GAG ACT GAC GAA TTT CTG AAA CCA ATT GTT TTT TCG GAC GAT GGG CGA GTA AAA GAT GAC
E   T   D   E   F   L   K   P   I   V   F   S   D   D   G   R   V   K   D   D
781
GAT ACT CTT ATT TTC TTC AAT TAT CGT GCT GAT CGT ATG CGT CAA ATT TGT GAA TGT TTG
D   T   L   I   F   F   N   Y   R   A   D   R   M   R   Q   I   C   E   C   L
841
GGT CTC GAA CGT TAT AAA GAT CTT AAT AGT TCG GTT CCT CAC CCT AAA AAT ATT CAG ATT
G   L   E   R   Y   K   D   L   N   S   S   V   P   H   P   K   N   I   Q   I
```

FIGURE 1A

```
901
AGT GGG ATG ACC CAA TAC AAT AAA GAG TTT CCA TTT CCA TCG TTA TTC CCA CCT GTG ACT
 S   G   M   T   Q   Y   N   K   E   F   P   F   P   S   L   F   P   P   V   T
961
CAT ACT AAT GTG CTT GCT GAA TGG CTT GCT TCT CAA GGA GTT ACT CAA TTT CAC TGT GCG
 H   T   N   V   L   A   E   W   L   A   S   Q   G   V   T   Q   F   H   C   A
1021
GAA ACT GAG AAG TAT CCT CAT GTT ACC TTC TTC TTT AAT GGT GGT CGA GAA GTT CAA TTC
 E   T   E   K   Y   P   H   V   T   F   F   F   N   G   G   R   E   V   Q   F
1081
CAA GAT GAA GAG CGT TGT ATG GTT CCG TCA CCA AAA GAA GTT GCT ACA TAT GAT TTA AAA
 Q   D   E   E   R   C   M   V   P   S   P   K   E   V   A   T   Y   D   L   K
1141
CCA GAA ATG AAT GCT GCT GGA GTT GCC GAA AAA ATG GTC GAG CAA ATT GAG TCA GGC AGG
 P   E   M   N   A   A   G   V   A   E   K   M   V   E   Q   I   E   S   G   R
1201
CAT CCT TTG GTT ATG TGC AAT TTT GCG CCT CCT GAC ATG GTT GGA CAT ACT GGT AAA TTT
 H   P   L   V   M   C   N   F   A   P   P   D   M   V   G   H   T   G   K   F
1261
GAA CCT GCC GTC AAA GCA TGT CAA GCT ACT GAC GAG GCA ATT GGA AAG ATA TTT GAA GCA
 E   P   A   V   K   A   C   Q   A   T   D   E   A   I   G   K   I   F   E   A
1321
TGC CAA ACT TAT AAT TAC GTT CTT ATG GTT ACT TCC GAT CAT GGA AAT GCT GAG AAG ATG
 C   Q   T   Y   N   Y   V   L   M   V   T   S   D   H   G   N   A   E   K   M
1381
ATT GCT CCC GAT GGT AGT GAA CAT ACT GCA CAT ACC TGC AAT TTG GTC CCA TTT ACT TGC
 I   A   P   D   G   S   E   H   T   A   H   T   C   N   L   V   P   F   T   C
1441
TCT TCC AAA ACA TTT GTT TTT AAA TCG ACT CCA CCT ACT GGA GAT GAT GGC AAA GAA CGT
 S   S   K   T   F   V   F   K   S   T   P   P   T   G   D   D   G   K   E   R
1501
GCA CGA GCC TTA CGT GAT GTT GCA CCG ACT GTT CTA CAA TTA ATG GGC TTA CCT GTA CCG
 A   R   A   L   R   D   V   A   P   T   V   L   Q   L   M   G   L   P   V   P
1561
CCG GAG ATG GAT GGC GTT CCT TTA CTT GAA CAG AGA GGA TAA gaa gtt aat tga caa tag
 P   E   M   D   G   V   P   L   L   E   Q   R   G   *
1621
gaa ata aat atg agc tgc tat tac aag caa ttt taa aaa ttt tag taa aac gag taa ttt 1681
ttg ata tat aca tat tta gaa atc tcc gtt ata aaa att
```

FIGURE 1B

```
1
Met phe val ala leu gly ala gln ile tyr arg gln tyr phe gly arg arg gly met ala
21
met ala asn asn ser ser val ala asn lys val cys leu ile val ile asp gly trp gly
41
val ser glu asp pro tyr gly asn ala ile leu asn ala gln thr pro val met asp lys
61
leu cys ser gly asn trp ala gln ile glu ala his gly leu his val gly leu pro glu
81
gly leu met gly asn ser glu val gly his leu asn ile gly ala gly arg val ile tyr
101
gln asp ile val arg ile asn leu ala val lys asn asn lys phe val thr asn glu ser
121
leu val asp ala cys asp arg ala lys asn gly asn gly arg leu his leu ala gly leu
141
val ser asp gly gly val his ser his ile asp his met phe ala leu val lys ala ile
161
lys glu leu gly val pro glu leu tyr leu his phe tyr gly asp gly arg asp thr ser
181
pro asn ser gly val gly phe leu glu gln thr leu glu phe leu glu lys thr thr gly
201
tyr gly lys leu ala thr val val gly arg tyr tyr ala met asp arg asp asn arg trp
221
glu arg ile asn val ala tyr glu ala met ile gly gly val gly glu thr ser asp glu
241
ala gly val val glu val val arg lys arg tyr ala ala asp glu thr asp glu phe leu
261
lys pro ile ile leu gln gly glu lys gly arg val gln asn asp asp thr ile ile phe
281
phe asp tyr arg ala asp arg met arg glu ile ser ala ala met gly met asp arg tyr
301
lys asp cys asn ser lys leu ala his pro ser asn leu gln val tyr gly met thr gln
321
tyr lys ala glu phe pro phe lys ser leu phe pro pro ala ser asn lys asn val leu
341
ala glu trp leu ala glu gln lys val ser gln phe his cys ala glu thr glu lys tyr
361
ala his val thr phe phe phe asn gly gly leu glu lys gln phe glu gly glu glu arg
381
cys leu val pro ser pro lys val ala thr tyr asp leu gln pro glu met ser ala ala
401
gly val ala asp lys met ile glu gln leu glu ala gly thr his pro phe ile met cys
421
asn phe ala pro pro asp met val gly his thr gly val tyr glu ala ala val lys ala
441
cys glu ala thr asp ile ala ile gly arg ile tyr glu ala thr gln lys his gly tyr
```

FIGURE 2A

```
461
ser leu met val thr ala asp his gly asn ala glu lys met lys ala pro asp gly gly
481
lys his thr ala his thr cys tyr arg val pro leu thr leu ser his pro gly phe lys
501
phe val asp pro ala asp arg his pro ala leu cys asp val ala pro thr val leu ala
521
ile met gly leu pro gln pro ala glu met thr gly val ser ile val gln lys ile
```

FIGURE 2B

1 *M.incognita* PGM
2 *C.elegans* PGM

```
1  ..................MDKYQNMQ............................H........K.K......: 40
2  MFVALGAQIYRQYFGRRGMA.ANNSS.A..................PY.....LN.Q........: 60

1  ..C.N..QK.............................................QR.E......PQ:100
2  ...GN.AQ.......................................KN.K...ES:120

1  ..ASA...K.S...L................F.Q.Q..K.........:160
2  ..DAC..........A..................I.E.G.E............:180

1  .T..A......L..Q...ASEK..GE...T........K.....KM..........QKATV:219
2  .N.....T.E..EKTTG..K......V..........N......N..........ETSDE:240

1  DKA.....E...QS.........FS..DD..MKD.........N.........Q.CEC.....:278
2  AGV........AD.............LQG.K...QN.........D.........E.SAA....:300

1  ..L..S.P..K.....S......NK......PG.....V.HT..........S.G......... :338
2  ...K.A..S....Y.....KA.....KS.....ASNK.........E.K...........:360

1  P......NG.R.V..QD......................K..N............S.R..L..:398
2  A..................K..EG..............Q...S.....................A.T..F.:419

1  .N...........K.S.P......Q..DE.........C.TYN.V......S..........I....:458
2  ............V..A.....E....I.........T.KHG..S.....A............K...:479

1  SE.......NL..F..C.SKT.V.KSTPPTGDDGK...AR..R..........Q.M...V.P..D.:518
2  GK........YR....L.HPG.K..VDP.......A...HP..C........A........Q.A..T.:532

1  .P...EQRG:526
2  .S...QKIZ:539
```

FIGURE 3

SEQUENCE LISTING

<160> NUMBER OF SEQ ID NOS: 14

<210> SEQ ID NO 1
<211> LENGTH: 1719
<212> TYPE: DNA
<213> ORGANISM: Meloidogyne incognita PGM
<220> FEATURE:
<221> NAME/KEY: CDS
<222> LOCATION: (22)...(1599)

<400> SEQUENCE: 1

```
gtttaattac ccaagtttga g atg gac aaa tat caa aat gtt caa caa aaa        51
                        Met Asp Lys Tyr Gln Asn Val Gln Gln Lys
                         1               5                      10 gtc tgt ctt gta gtt att gat gga tgg ggc ctt tcc gat gaa caa cac        99
Val Cys Leu Val Val Ile Asp Gly Trp Gly Leu Ser Asp Glu Gln His
                 15                  20                  25 ggg aat gca att gct aaa gct aaa acg cct att atg gac aaa ctt tgt       147
Gly Asn Ala Ile Ala Lys Ala Lys Thr Pro Ile Met Asp Lys Leu Cys
             30                  35                  40 tct gga aat tgg caa aaa ttg gaa gca cac ggt ctt cat gtt gga ttg       195
Ser Gly Asn Trp Gln Lys Leu Glu Ala His Gly Leu His Val Gly Leu
         45                  50                  55 cca gaa ggc tta atg gga aat tct gaa gtt gga cat ttg aat ata gga       243
Pro Glu Gly Leu Met Gly Asn Ser Glu Val Gly His Leu Asn Ile Gly
     60                  65                  70 gct gga aga gtt att tat caa gat att gtt cga att aat ttg gct gtt       291
Ala Gly Arg Val Ile Tyr Gln Asp Ile Val Arg Ile Asn Leu Ala Val
 75                  80                  85                  90 caa cga aac gag ttt gtt aca aat cct cag att gtt gca tca gct gag       339
Gln Arg Asn Glu Phe Val Thr Asn Pro Gln Ile Val Ala Ser Ala Glu
                 95                 100                 105 cgt gca aag aag ggg agt ggt cga ttg cat tta tta gga ctg gtt agc       387
Arg Ala Lys Lys Gly Ser Gly Arg Leu His Leu Leu Gly Leu Val Ser
            110                 115                 120 gat ggt ggt gtc cac tct cat att gat cat ctt ttt gcg ttg ata cgt       435
Asp Gly Gly Val His Ser His Ile Asp His Leu Phe Ala Leu Ile Arg
        125                 130                 135 gca ttt aaa caa tta caa gtg cca aag gtt ttc att cac ttt ttt gct       483
Ala Phe Lys Gln Leu Gln Val Pro Lys Val Phe Ile His Phe Phe Ala
    140                 145                 150 gat ggt cga gat act tcg cca aca agt gga gct ggt tat ctt gaa caa       531
Asp Gly Arg Asp Thr Ser Pro Thr Ser Gly Ala Gly Tyr Leu Glu Gln
155                 160                 165                 170
```

|     |     |     |     |     |     |     |     |     |     |     |     |     |     |     |     | |
|---|---|---|---|---|---|---|---|---|---|---|---|---|---|---|---|---|
| ctt | ctt | caa | ttt | att | gct | tcg | gaa | aag | tac | gga | gaa | ttg | gct | act | att | 579 |
| Leu | Leu | Gln | Phe | Ile | Ala | Ser | Glu | Lys | Tyr | Gly | Glu | Leu | Ala | Thr | Ile | |
|     |     |     |     | 175 |     |     |     |     | 180 |     |     |     |     | 185 |     | |
| act | gga | cgt | tat | tat | gca | atg | gat | agg | gac | aaa | aga | tgg | gag | cgt | att | 627 |
| Thr | Gly | Arg | Tyr | Tyr | Ala | Met | Asp | Arg | Asp | Lys | Arg | Trp | Glu | Arg | Ile | |
|     |     |     | 190 |     |     |     |     | 195 |     |     |     |     | 200 |     |     | |
| aag | atg | gct | tat | gag | gca | att | gtt | gga | ggt | att | gga | caa | aaa | gcc | acc | 675 |
| Lys | Met | Ala | Tyr | Glu | Ala | Ile | Val | Gly | Gly | Ile | Gly | Gln | Lys | Ala | Thr | |
|     |     | 205 |     |     |     |     | 210 |     |     |     |     | 215 |     |     |     | |
| gtt | gat | aag | gct | gtc | gat | gtt | gtt | aga | gag | cga | tat | gct | caa | tct | gag | 723 |
| Val | Asp | Lys | Ala | Val | Asp | Val | Val | Arg | Glu | Arg | Tyr | Ala | Gln | Ser | Glu | |
|     | 220 |     |     |     | 225 |     |     |     |     | 230 |     |     |     |     |     | |
| act | gac | gaa | ttt | ctg | aaa | cca | att | gtt | ttt | tcg | gac | gat | ggg | cga | gta | 771 |
| Thr | Asp | Glu | Phe | Leu | Lys | Pro | Ile | Val | Phe | Ser | Asp | Asp | Gly | Arg | Val | |
| 235 |     |     |     | 240 |     |     |     |     | 245 |     |     |     |     | 250 |     | |
| aaa | gat | gac | gat | act | ctt | att | ttc | ttc | aat | tat | cgt | gct | gat | cgt | atg | 819 |
| Lys | Asp | Asp | Asp | Thr | Leu | Ile | Phe | Phe | Asn | Tyr | Arg | Ala | Asp | Arg | Met | |
|     |     |     |     | 255 |     |     |     |     | 260 |     |     |     |     | 265 |     | |
| cgt | caa | att | tgt | gaa | tgt | ttg | ggt | ctc | gaa | cgt | tat | aaa | gat | ctt | aat | 867 |
| Arg | Gln | Ile | Cys | Glu | Cys | Leu | Gly | Leu | Glu | Arg | Tyr | Lys | Asp | Leu | Asn | |
|     |     |     | 270 |     |     |     |     | 275 |     |     |     |     | 280 |     |     | |
| agt | tcg | gtt | cct | cac | cct | aaa | aat | att | cag | att | agt | ggg | atg | acc | caa | 915 |
| Ser | Ser | Val | Pro | His | Pro | Lys | Asn | Ile | Gln | Ile | Ser | Gly | Met | Thr | Gln | |
|     |     | 285 |     |     |     |     | 290 |     |     |     |     | 295 |     |     |     | |
| tac | aat | aaa | gag | ttt | cca | ttt | cca | tcg | tta | ttc | cca | cct | gtg | act | cat | 963 |
| Tyr | Asn | Lys | Glu | Phe | Pro | Phe | Pro | Ser | Leu | Phe | Pro | Pro | Val | Thr | His | |
|     | 300 |     |     |     |     | 305 |     |     |     |     | 310 |     |     |     |     | |
| act | aat | gtg | ctt | gct | gaa | tgg | ctt | gct | tct | caa | gga | gtt | act | caa | ttt | 1011 |
| Thr | Asn | Val | Leu | Ala | Glu | Trp | Leu | Ala | Ser | Gln | Gly | Val | Thr | Gln | Phe | |
| 315 |     |     |     | 320 |     |     |     |     | 325 |     |     |     |     | 330 |     | |
| cac | tgt | gcg | gaa | act | gag | aag | tat | cct | cat | gtt | acc | ttc | ttc | ttt | aat | 1059 |
| His | Cys | Ala | Glu | Thr | Glu | Lys | Tyr | Pro | His | Val | Thr | Phe | Phe | Phe | Asn | |
|     |     |     |     | 335 |     |     |     |     | 340 |     |     |     |     | 345 |     | |
| ggt | ggt | cga | gaa | gtt | caa | ttc | caa | gat | gaa | gag | cgt | tgt | atg | gtt | ccg | 1107 |
| Gly | Gly | Arg | Glu | Val | Gln | Phe | Gln | Asp | Glu | Glu | Arg | Cys | Met | Val | Pro | |
|     |     |     | 350 |     |     |     |     | 355 |     |     |     |     | 360 |     |     | |
| tca | cca | aaa | gaa | gtt | gct | aca | tat | gat | tta | aaa | cca | gaa | atg | aat | gct | 1155 |
| Ser | Pro | Lys | Glu | Val | Ala | Thr | Tyr | Asp | Leu | Lys | Pro | Glu | Met | Asn | Ala | |
|     |     | 365 |     |     |     |     | 370 |     |     |     |     | 375 |     |     |     | |
| gct | gga | gtt | gcc | gaa | aaa | atg | gtc | gag | caa | att | gag | tca | ggc | agg | cat | 1203 |
| Ala | Gly | Val | Ala | Glu | Lys | Met | Val | Glu | Gln | Ile | Glu | Ser | Gly | Arg | His | |
|     | 380 |     |     |     |     | 385 |     |     |     |     | 390 |     |     |     |     | |
| cct | ttg | gtt | atg | tgc | aat | ttt | gcg | cct | cct | gac | atg | gtt | gga | cat | act | 1251 |
| Pro | Leu | Val | Met | Cys | Asn | Phe | Ala | Pro | Pro | Asp | Met | Val | Gly | His | Thr | |
| 395 |     |     |     | 400 |     |     |     |     | 405 |     |     |     |     | 410 |     | |
| ggt | aaa | ttt | gaa | cct | gcc | gtc | aaa | gca | tgt | caa | gct | act | gac | gag | gca | 1299 |
| Gly | Lys | Phe | Glu | Pro | Ala | Val | Lys | Ala | Cys | Gln | Ala | Thr | Asp | Glu | Ala | |
|     |     |     |     | 415 |     |     |     |     | 420 |     |     |     |     | 425 |     | |
| att | gga | aag | ata | ttt | gaa | gca | tgc | caa | act | tat | aat | tac | gtt | ctt | atg | 1347 |
| Ile | Gly | Lys | Ile | Phe | Glu | Ala | Cys | Gln | Thr | Tyr | Asn | Tyr | Val | Leu | Met | |
|     |     |     | 430 |     |     |     |     | 435 |     |     |     |     | 440 |     |     | |
| gtt | act | tcc | gat | cat | gga | aat | gct | gag | aag | atg | att | gct | ccc | gat | ggt | 1395 |
| Val | Thr | Ser | Asp | His | Gly | Asn | Ala | Glu | Lys | Met | Ile | Ala | Pro | Asp | Gly | |
|     |     |     | 445 |     |     |     |     | 450 |     |     |     |     | 455 |     |     | |
| agt | gaa | cat | act | gca | cat | acc | tgc | aat | ttg | gtc | cca | ttt | act | tgc | tct | 1443 |
| Ser | Glu | His | Thr | Ala | His | Thr | Cys | Asn | Leu | Val | Pro | Phe | Thr | Cys | Ser | |
|     |     |     | 460 |     |     |     |     | 465 |     |     |     |     | 470 |     |     | |
| tcc | aaa | aca | ttt | gtt | ttt | aaa | tcg | act | cca | cct | act | gga | gat | gat | ggc | 1491 |
| Ser | Lys | Thr | Phe | Val | Phe | Lys | Ser | Thr | Pro | Pro | Thr | Gly | Asp | Asp | Gly | |
| 475 |     |     |     | 480 |     |     |     |     | 485 |     |     |     |     | 490 |     | |

-continued

```
aaa gaa cgt gca cga gcc tta cgt gat gtt gca ccg act gtt cta caa   1539
Lys Glu Arg Ala Arg Ala Leu Arg Asp Val Ala Pro Thr Val Leu Gln
            495                 500                 505 tta atg ggc tta cct gta ccg ccg gag atg gat ggc gtt cct tta ctt   1587
Leu Met Gly Leu Pro Val Pro Pro Glu Met Asp Gly Val Pro Leu Leu
            510                 515                 520 gaa cag aga gga taagaagtta attgacaata ggaaataaat atgagctgct       1639
Glu Gln Arg Gly
            525 attacaagca attttaaaaa ttttagtaaa acgagtaatt tttgatatat acatatttag 1699 aaatctccgt tataaaaatt                                             1719
```

<210> SEQ ID NO 2
<211> LENGTH: 526
<212> TYPE: PRT
<213> ORGANISM: Meloidogyne incognita PGM

<400> SEQUENCE: 2

```
Met Asp Lys Tyr Gln Asn Val Gln Gln Lys Val Cys Leu Val Val Ile
  1               5                  10                  15

Asp Gly Trp Gly Leu Ser Asp Glu Gln His Gly Asn Ala Ile Ala Lys
             20                  25                  30

Ala Lys Thr Pro Ile Met Asp Lys Leu Cys Ser Gly Asn Trp Gln Lys
         35                  40                  45

Leu Glu Ala His Gly Leu His Val Gly Leu Pro Glu Gly Leu Met Gly
     50                  55                  60

Asn Ser Glu Val Gly His Leu Asn Ile Gly Ala Gly Arg Val Ile Tyr
 65                  70                  75                  80

Gln Asp Ile Val Arg Ile Asn Leu Ala Val Gln Arg Asn Glu Phe Val
                 85                  90                  95

Thr Asn Pro Gln Ile Val Ala Ser Ala Glu Arg Ala Lys Lys Gly Ser
            100                 105                 110

Gly Arg Leu His Leu Leu Gly Leu Val Ser Asp Gly Gly Val His Ser
        115                 120                 125

His Ile Asp His Leu Phe Ala Leu Ile Arg Ala Phe Lys Gln Leu Gln
    130                 135                 140

Val Pro Lys Val Phe Ile His Phe Phe Ala Asp Gly Arg Asp Thr Ser
145                 150                 155                 160

Pro Thr Ser Gly Ala Gly Tyr Leu Glu Gln Leu Leu Gln Phe Ile Ala
                165                 170                 175

Ser Glu Lys Tyr Gly Glu Leu Ala Thr Ile Thr Gly Arg Tyr Tyr Ala
            180                 185                 190

Met Asp Arg Asp Lys Arg Trp Glu Arg Ile Lys Met Ala Tyr Glu Ala
        195                 200                 205

Ile Val Gly Gly Ile Gly Gln Lys Ala Thr Val Asp Lys Ala Val Asp
    210                 215                 220

Val Val Arg Glu Arg Tyr Ala Gln Ser Glu Thr Asp Glu Phe Leu Lys
225                 230                 235                 240

Pro Ile Val Phe Ser Asp Gly Arg Val Lys Asp Asp Thr Leu
                245                 250                 255

Ile Phe Phe Asn Tyr Arg Ala Asp Arg Met Arg Gln Ile Cys Glu Cys
            260                 265                 270

Leu Gly Leu Glu Arg Tyr Lys Asp Leu Asn Ser Ser Val Pro His Pro
        275                 280                 285
```

-continued

```
Lys Asn Ile Gln Ile Ser Gly Met Thr Gln Tyr Asn Lys Glu Phe Pro
    290                 295                 300

Phe Pro Ser Leu Phe Pro Pro Val Thr His Thr Asn Val Leu Ala Glu
305                 310                 315                 320

Trp Leu Ala Ser Gln Gly Val Thr Gln Phe His Cys Ala Glu Thr Glu
                325                 330                 335

Lys Tyr Pro His Val Thr Phe Phe Asn Gly Gly Arg Glu Val Gln
                340                 345                 350

Phe Gln Asp Glu Glu Arg Cys Met Val Pro Ser Pro Lys Glu Val Ala
            355                 360                 365

Thr Tyr Asp Leu Lys Pro Glu Met Asn Ala Ala Gly Val Ala Glu Lys
        370                 375                 380

Met Val Glu Gln Ile Glu Ser Gly Arg His Pro Leu Val Met Cys Asn
385                 390                 395                 400

Phe Ala Pro Pro Asp Met Val Gly His Thr Gly Lys Phe Glu Pro Ala
                405                 410                 415

Val Lys Ala Cys Gln Ala Thr Asp Glu Ala Ile Gly Lys Ile Phe Glu
                420                 425                 430

Ala Cys Gln Thr Tyr Asn Tyr Val Leu Met Val Thr Ser Asp His Gly
            435                 440                 445

Asn Ala Glu Lys Met Ile Ala Pro Asp Gly Ser Glu His Thr Ala His
        450                 455                 460

Thr Cys Asn Leu Val Pro Phe Thr Cys Ser Ser Lys Thr Phe Val Phe
465                 470                 475                 480

Lys Ser Thr Pro Pro Thr Gly Asp Asp Gly Lys Glu Arg Ala Arg Ala
                485                 490                 495

Leu Arg Asp Val Ala Pro Thr Val Leu Gln Leu Met Gly Leu Pro Val
            500                 505                 510

Pro Pro Glu Met Asp Gly Val Pro Leu Leu Glu Gln Arg Gly
        515                 520                 525

<210> SEQ ID NO 3
<211> LENGTH: 539
<212> TYPE: PRT
<213> ORGANISM: Caenorhabiditis elegans PGM

<400> SEQUENCE: 3

Met Phe Val Ala Leu Gly Ala Gln Ile Tyr Arg Gln Tyr Phe Gly Arg
1               5                   10                  15

Arg Gly Met Ala Met Ala Asn Asn Ser Ser Val Ala Asn Lys Val Cys
            20                  25                  30

Leu Ile Val Ile Asp Gly Trp Gly Val Ser Glu Asp Pro Tyr Gly Asn
        35                  40                  45

Ala Ile Leu Asn Ala Gln Thr Pro Val Met Asp Lys Leu Cys Ser Gly
    50                  55                  60

Asn Trp Ala Gln Ile Glu Ala His Gly Leu His Val Gly Leu Pro Glu
65              70                  75                  80

Gly Leu Met Gly Asn Ser Glu Val Gly His Leu Asn Ile Gly Ala Gly
                85                  90                  95

Arg Val Ile Tyr Gln Asp Ile Val Arg Ile Asn Leu Ala Val Lys Asn
            100                 105                 110

Asn Lys Phe Val Thr Asn Glu Ser Leu Val Asp Ala Cys Asp Arg Ala
        115                 120                 125

Lys Asn Gly Asn Gly Arg Leu His Leu Ala Gly Leu Val Ser Asp Gly
    130                 135                 140
```

```
Gly Val His Ser His Ile Asp His Met Phe Ala Leu Val Lys Ala Ile
145                 150                 155                 160

Lys Glu Leu Gly Val Pro Glu Leu Tyr Leu His Phe Tyr Gly Asp Gly
                165                 170                 175

Arg Asp Thr Ser Pro Asn Ser Gly Val Gly Phe Leu Glu Gln Thr Leu
            180                 185                 190

Glu Phe Leu Glu Lys Thr Thr Gly Tyr Gly Lys Leu Ala Thr Val Val
        195                 200                 205

Gly Arg Tyr Tyr Ala Met Asp Arg Asp Asn Arg Trp Glu Arg Ile Asn
    210                 215                 220

Val Ala Tyr Glu Ala Met Ile Gly Gly Val Gly Glu Thr Ser Asp Glu
225                 230                 235                 240

Ala Gly Val Val Glu Val Arg Lys Arg Tyr Ala Ala Asp Glu Thr
                245                 250                 255

Asp Glu Phe Leu Lys Pro Ile Ile Leu Gln Gly Glu Lys Gly Arg Val
            260                 265                 270

Gln Asn Asp Asp Thr Ile Ile Phe Phe Asp Tyr Arg Ala Asp Arg Met
        275                 280                 285

Arg Glu Ile Ser Ala Ala Met Gly Met Asp Arg Tyr Lys Asp Cys Asn
    290                 295                 300

Ser Lys Leu Ala His Pro Ser Asn Leu Gln Val Tyr Gly Met Thr Gln
305                 310                 315                 320

Tyr Lys Ala Glu Phe Pro Phe Lys Ser Leu Phe Pro Pro Ala Ser Asn
                325                 330                 335

Lys Asn Val Leu Ala Glu Trp Leu Ala Glu Lys Val Ser Gln Phe
            340                 345                 350

His Cys Ala Glu Thr Glu Lys Tyr Ala His Val Thr Phe Phe Asn
        355                 360                 365

Gly Gly Leu Glu Lys Gln Phe Glu Gly Glu Arg Cys Leu Val Pro
    370                 375                 380

Ser Pro Lys Val Ala Thr Tyr Asp Leu Gln Pro Glu Met Ser Ala Ala
385                 390                 395                 400

Gly Val Ala Asp Lys Met Ile Glu Gln Leu Glu Ala Gly Thr His Pro
                405                 410                 415

Phe Ile Met Cys Asn Phe Ala Pro Pro Asp Met Val Gly His Thr Gly
            420                 425                 430

Val Tyr Glu Ala Ala Val Lys Ala Cys Glu Ala Thr Asp Ile Ala Ile
        435                 440                 445

Gly Arg Ile Tyr Glu Ala Thr Gln Lys His Gly Tyr Ser Leu Met Val
    450                 455                 460

Thr Ala Asp His Gly Asn Ala Glu Lys Met Lys Ala Pro Asp Gly Gly
465                 470                 475                 480

Lys His Thr Ala His Thr Cys Tyr Arg Val Pro Leu Thr Leu Ser His
                485                 490                 495

Pro Gly Phe Lys Phe Val Asp Pro Ala Asp Arg His Pro Ala Leu Cys
            500                 505                 510

Asp Val Ala Pro Thr Val Leu Ala Ile Met Gly Leu Pro Gln Pro Ala
        515                 520                 525

Glu Met Thr Gly Val Ser Ile Val Gln Lys Ile
530                 535

<210> SEQ ID NO 4
<211> LENGTH: 526
```

```
<212> TYPE: PRT
<213> ORGANISM: Meloidogyne icognita PGM

<400> SEQUENCE: 4

Met Asp Lys Tyr Gln Asn Val Gln Gln Lys Val Cys Leu Val Val Ile
1               5                   10                  15

Asp Gly Trp Gly Leu Ser Asp Glu Gln His Gly Asn Ala Ile Ala Lys
            20                  25                  30

Ala Lys Thr Pro Ile Met Asp Lys Leu Cys Ser Gly Asn Trp Gln Lys
        35                  40                  45

Leu Glu Ala His Gly Leu His Val Gly Leu Pro Glu Gly Leu Met Gly
    50                  55                  60

Asn Ser Glu Val Gly His Leu Asn Ile Gly Ala Gly Arg Val Ile Tyr
65                  70                  75                  80

Gln Asp Ile Val Arg Ile Asn Leu Ala Val Gln Arg Asn Glu Phe Val
                85                  90                  95

Thr Asn Pro Gln Ile Val Ala Ser Ala Glu Arg Ala Lys Lys Gly Ser
            100                 105                 110

Gly Arg Leu His Leu Leu Gly Leu Val Ser Asp Gly Gly Val His Ser
        115                 120                 125

His Ile Asp His Leu Phe Ala Leu Ile Arg Ala Phe Lys Gln Leu Gln
    130                 135                 140

Val Pro Lys Val Phe Ile His Phe Phe Ala Asp Gly Arg Asp Thr Ser
145                 150                 155                 160

Pro Thr Ser Gly Ala Gly Tyr Leu Glu Gln Leu Leu Gln Phe Ile Ala
                165                 170                 175

Ser Glu Lys Tyr Gly Glu Leu Ala Thr Ile Thr Gly Arg Tyr Tyr Ala
            180                 185                 190

Met Asp Arg Asp Lys Arg Trp Glu Arg Ile Lys Met Ala Tyr Glu Ala
        195                 200                 205

Ile Val Gly Gly Ile Gly Gln Lys Ala Thr Val Asp Lys Ala Val Asp
    210                 215                 220

Val Val Arg Glu Arg Tyr Ala Gln Ser Glu Thr Asp Glu Phe Leu Lys
225                 230                 235                 240

Pro Ile Val Phe Ser Asp Asp Gly Arg Val Lys Asp Asp Thr Leu
                245                 250                 255

Ile Phe Phe Asn Tyr Arg Ala Asp Arg Met Arg Gln Ile Cys Glu Cys
            260                 265                 270

Leu Gly Leu Glu Arg Tyr Lys Asp Leu Asn Ser Ser Val Pro His Pro
        275                 280                 285

Lys Asn Ile Gln Ile Ser Gly Met Thr Gln Tyr Asn Lys Glu Phe Pro
    290                 295                 300

Phe Pro Ser Leu Phe Pro Pro Val Thr His Thr Asn Val Leu Ala Glu
305                 310                 315                 320

Trp Leu Ala Ser Gln Gly Val Thr Gln Phe His Cys Ala Glu Thr Glu
                325                 330                 335

Lys Tyr Pro His Val Thr Phe Phe Asn Gly Gly Arg Glu Val Gln
            340                 345                 350

Phe Gln Asp Glu Glu Arg Cys Met Val Pro Ser Pro Lys Glu Val Ala
        355                 360                 365

Thr Tyr Asp Leu Lys Pro Glu Met Asn Ala Ala Gly Val Ala Glu Lys
    370                 375                 380

Met Val Glu Gln Ile Glu Ser Gly Arg His Pro Leu Val Met Cys Asn
385                 390                 395                 400
```

-continued

```
Phe Ala Pro Pro Asp Met Val Gly His Thr Gly Lys Phe Glu Pro Ala
            405                 410                 415
Val Lys Ala Cys Gln Ala Thr Asp Glu Ala Ile Gly Lys Ile Phe Glu
            420                 425                 430
Ala Cys Gln Thr Tyr Asn Tyr Val Leu Met Val Thr Ser Asp His Gly
            435                 440                 445
Asn Ala Glu Lys Met Ile Ala Pro Asp Gly Ser Glu His Thr Ala His
450                 455                 460
Thr Cys Asn Leu Val Pro Phe Thr Cys Ser Ser Lys Thr Phe Val Phe
465                 470                 475                 480
Lys Ser Thr Pro Pro Thr Gly Asp Asp Gly Lys Glu Arg Ala Arg Ala
            485                 490                 495
Leu Arg Asp Val Ala Pro Thr Val Leu Gln Leu Met Gly Leu Pro Val
            500                 505                 510
Pro Pro Glu Met Asp Gly Val Pro Leu Leu Glu Gln Arg Gly
            515                 520                 525
```

```
<210> SEQ ID NO 5
<211> LENGTH: 22
<212> TYPE: DNA
<213> ORGANISM: Artificial Sequence
<220> FEATURE:
<223> OTHER INFORMATION: Vector polylinker primer

<400> SEQUENCE: 5
gtaatacgac tcactatagg gc                                              22

<210> SEQ ID NO 6
<211> LENGTH: 20
<212> TYPE: DNA
<213> ORGANISM: Artificial Sequence
<220> FEATURE:
<223> OTHER INFORMATION: Vector polylinker primer

<400> SEQUENCE: 6
aattaaccct cactaaaggg                                                 20

<210> SEQ ID NO 7
<211> LENGTH: 50
<212> TYPE: DNA
<213> ORGANISM: Artificial Sequence
<220> FEATURE:
<223> OTHER INFORMATION: Univeral primer to poly A tail

<400> SEQUENCE: 7
gagagagaga gagagagaga actagtctcg agtttttttt tttttttttt                50

<210> SEQ ID NO 8
<211> LENGTH: 22
<212> TYPE: DNA
<213> ORGANISM: Artificial Sequence
<220> FEATURE:
<223> OTHER INFORMATION: Nematode transpliced leader

<400> SEQUENCE: 8
gggtttaatt acccaagttt ga                                              22

<210> SEQ ID NO 9
<211> LENGTH: 18
<212> TYPE: DNA
<213> ORGANISM: Artificial Sequence
<220> FEATURE:
```

```
<223> OTHER INFORMATION: Mi PGM (codon 234-239)

<400> SEQUENCE: 9
gagactgacg aatttctg                                                    18

<210> SEQ ID NO 10
<211> LENGTH: 18
<212> TYPE: DNA
<213> ORGANISM: Artificial Sequence
<220> FEATURE:
<223> OTHER INFORMATION: Mi PGM (codon 234-239)

<400> SEQUENCE: 10
cagaaattcg tcagtctc                                                    18

<210> SEQ ID NO 11
<211> LENGTH: 17
<212> TYPE: DNA
<213> ORGANISM: Artificial Sequence
<220> FEATURE:
<223> OTHER INFORMATION: Mi PGM (codon 15-20)

<400> SEQUENCE: 11
gttattgatg gatgggg                                                     17

<210> SEQ ID NO 12
<211> LENGTH: 17
<212> TYPE: DNA
<213> ORGANISM: Artificial Sequence
<220> FEATURE:
<223> OTHER INFORMATION: Mi PGM (codon 15-20)

<400> SEQUENCE: 12
ccccatccat caataac                                                     17

<210> SEQ ID NO 13
<211> LENGTH: 20
<212> TYPE: DNA
<213> ORGANISM: Artificial Sequence
<220> FEATURE:
<223> OTHER INFORMATION: Mi PGM (codon 59-65)

<400> SEQUENCE: 13
ccagaaggct taatgggaaa                                                  20

<210> SEQ ID NO 14
<211> LENGTH: 20
<212> TYPE: DNA
<213> ORGANISM: Artificial Sequence
<220> FEATURE:
<223> OTHER INFORMATION: Mi PGM (codon 59-65)

<400> SEQUENCE: 14
tttcccatta agccttctgg                                                  20
```

NEMATODE PGM-LIKE SEQUENCES

RELATED APPLICATION INFORMATION

This application claims priority from provisional application Ser. No. 60/271,781, filed Feb. 27, 2001, the entire contents of which is hereby incorporated by reference.

BACKGROUND

Nematodes (derived from the Greek word for thread) are active, flexible, elongate, organisms that live on moist surfaces or in liquid environments, including films of water within soil and moist tissues within other organisms. While only 20,000 species of nematode have been identified, it is estimated that 40,000 to 10 million actually exist. Some species of nematodes have evolved as very successful parasites of both plants and animals and are responsible for significant economic losses in agriculture and livestock and for morbidity and mortality in humans (Whitehead (1998) *Plant Nematode Control*. CAB International, New York).

Nematode parasites of plants can inhabit all parts of plants, including roots, developing flower buds, leaves, and stems. Plant parasites are classified on the basis of their feeding habits into the broad categories: migratory ectoparasites, migratory endoparasites, and sedentary endoparasites. Sedentary endoparasites, which include the root knot nematodes (Meloidogyne) and cyst nematodes (Globodera and Heterodera) induce feeding sites and establish long-term infections within roots that are often very damaging to crops (Whitehead, supra). It is estimated that parasitic nematodes cost the horticulture and agriculture industries in excess of $78 billion worldwide a year, based on an estimated average 12% annual loss spread across all major crops. For example, it is estimated that nematodes cause soybean losses of approximately $3.2 billion annually worldwide (Barker et al. (1994) *Plant and Soil Nematodes: Societal Impact and Focus for the Future*. The Committee on National Needs and Priorities in Nematology. Cooperative State Research Service, US Department of Agriculture and Society of Nematologists). Several factors make the need for safe and effective nematode controls urgent. Continuing population growth, famines, and environmental degradation have heightened concern for the sustainability of agriculture, and new government regulations may prevent or severely restrict the use of many available agricultural anthelmintic agents.

The situation is particularly dire for high value crops such as strawberries and tomatoes where chemicals have been used extensively to control soil pests. The soil fumigant methyl bromide has been used effectively to reduce nematode infestations in a variety of these specialty crops. It is however regulated under the U.N. Montreal Protocol as an ozone-depleting substance and is scheduled for elimination in 2005 in the US (Carter (2001) *Califonia Agriculture*, 55(3):2). It is expected that strawberry and other commodity crop industries will be significantly impacted if a suitable replacement for methyl bromide is not found. Presently there are a very small array of chemicals available to control nematodes and they are frequently inadequate, unsuitable, or too costly for some crops or soils (Becker (1999) *Agricultural Research Magazine* 47(3):22–24; U.S. Pat. Nos. 6,048, 714). The few available broad-spectrum nematicides such as Telone (a mixture of 1,3-dichloropropene and chloropicrin) have significant restrictions on their use because of toxicological concerns (Carter (2001) *California Agriculture*, Vol. 55(3):12–18).

Fatty acids are a class of natural compounds that have been investigated as alternatives to the toxic, non-specific organophosphate, carbamate and fumigant pesticides (Stadler et al. (1994) *Planta Medica* 60(2):128–132; U.S. Pat. Nos. 5,192,546; 5,346,698; 5,674,897; 5,698,592; 6,124,359). It has been suggested that fatty acids derive their pesticidal effects by adversely interfering with the nematode cuticle or hypodermis via a detergent (solubilization) effect, or through direct interaction of the fatty acids and the lipophilic regions of target plasma membranes (Davis et al. (1997) *Journal of Nematology* 29(4S):677–684). In view of this general mode of action it is not surprising that fatty acids are used in a variety of pesticidal applications including as herbicides (e.g., SCYTHE by Dow Agrosciences is the C9 saturated fatty acid pelargonic acid), as bactericides and fungicides (U.S. Pat. Nos. 4,771,571; 5,246,716) and as insecticides (e.g., SAFER INSECTICIDAL SOAP by Safer, Inc.).

The phytotoxicity of fatty acids has been a major constraint on their general use in agricultural applications (U.S. Pat. No. 5,093,124) and the mitigation of these undesirable effects while preserving pesticidal activity is a major area of research. The esterification of fatty acids can significantly decrease their phytotoxicity (U.S. Pat. Nos. 5,674,897; 5,698,592; 6,124,359). Such modifications can however lead to dramatic loss of nematicidal activity as is seen for linoleic, linolenic and oleic acid (Stadler et al. (1994) *Planta Medica* 60(2):128–132) and it may be impossible to completely decouple the phytotoxicity and nematicidal activity of pesticidal fatty acids because of their non-specific mode of action. Perhaps not surprisingly, the nematicidal fatty acid pelargonic acid methyl ester (U.S. Pat. Nos. 5,674,897; 5,698,592; 6,124,359) shows a relatively small "therapeutic window" between the onset of pesticidal activity and the observation of significant phytotoxicity (Davis et al. (1997) *J Nematol* 29(4S):677–684). This is the expected result if both the phytotoxicity and the nematicidial activity derive from the non-specific disruption of plasma membrane integrity. Similarly the rapid onset of pesticidal activity seen with many nematicidal fatty acids at therapeutic concentrations (U.S. Pat. Nos. 5,674,897; 5,698,592; 6,124,359) suggests a non-specific mechanism of action, possibly related to the disruption of membranes, action potentials and neuronal activity.

Ricinoleic acid, the major component of castor oil, provides another example of the unexpected effects esterification can have on fatty acid activity. Ricinoleic acid has been shown to have an inhibitory effect on water and electrolyte absorption using everted hamster jejunal and ileal segments (Gaginella et al. (1975) *J Pharmacol Exp Ther* 195(2): 355–61) and to be cytotoxic to isolated intestinal epithelial cells (Gaginella et al. (1977) *J Pharmacol Exp Ther* 201(1): 259–66). These features are likely the source of the laxative properties of castor oil which is given as a purgative in humans and livestock. In contrast, the methyl ester of ricinoleic acid is ineffective at suppressing water absorption in the hamster model (Gaginella et al. (1975) *J Pharmacol Exp Ther* 195(2):355–61). (N.B. Castor oil is a component of some de-worming protocols because of its laxative properties.)

The macrocyclic lactones (e.g., avermectins and milbemycins) and delta-toxins from *Bacillus thuringiensis* (Bt) are chemicals that in principle provide excellent specificity and efficacy and should allow environmentally safe control of plant parasitic nematodes. Unfortunately, in practice, these two approaches have proven less effective for agricultural applications against root pathogens. Although certain avermectins show exquisite activity against plant parasitic nematodes these chemicals are hampered by poor bioavailability due to their light sensitivity, degradation by soil microorganisms and tight binding to soil particles (Lasota & Dybas (1990) *Acta Leiden* 59(1–2):217–225; Wright & Perry (1998) Musculature and Neurobiology. In: The Physiology and Biochemistry of Free-Living and Plant-parasitic Nematodes (eds R. N. Perry & D. J. Wright), CAB International 1998). Consequently despite years of research and extensive use against animal parasitic nematodes, mites and insects (plant and animal applications), macrocyclic lactones (e.g., avermectins and milbemycins) have never been commercially developed to control plant parasitic nematodes in the soil.

Bt delta toxins must be ingested to affect their target organ the brush border of midgut epithelial cells (Marroquin et al. (2000) *Genetics*. 155(4):1693–1699). Consequently they are not anticipated to be effective against the dispersal, non-feeding, juvenile stages of plant parasitic nematodes in the field. These juvenile stages only commence feeding when a susceptible host has been infected, thus to be effective nematicides may need to penetrate the cuticle. In addition, soil mobility of a relatively large 65–130 kDa protein—the size of typical Bt delta toxins—is expected to be poor and delivery in planta is likely to be constrained by the exclusion of large particles by the feeding tube of certain plant parasitic nematodes such as Heterodera (Atkinson et al. (1998) Engineering resistance to plant-parasitic nematodes. In: The Physiology and Biochemistry of Free-Living and Plant-parasitic Nematodes (eds R. N. Perry & D. J. Wright), CAB International 1998).

Many plant species are known to be highly resistant to nematodes. The most well documented of these include marigolds (Tagetes spp.), rattlebox (*Crotalaria spectabilis*), chrysanthemums (Chrysanthemum spp.), castor bean (*Ricinus communis*), margosa (*Azardiracta indica*), and many members of the family Asteraceae (family Compositae) (Hackney & Dickerson. (1975) *J Nematol* 7(1):84–90). The active principle(s) for this nematicidal activity has not been discovered in all of these examples and no plant-derived products are sold commercially for control of nematodes. In the case of the Asteraceae, the photodynamic compound alpha-terthienyl has been shown to account for the strong nematicidal activity of the roots. Castor beans are plowed under as a green manure before a seed crop is set However, a significant drawback of the castor plant is that the seed contains toxic compounds (such as ricin) that can kill humans, pets, and livestock and is also highly allergenic.

There remains an urgent need to develop environmentally safe, target-specific ways of controlling plant parasitic nematodes. In the specialty crop markets, economic hardship resulting from nematode infestation is highest in strawberries, bananas, and other high value vegetables and fruits. In the high-acreage crop markets, nematode damage is greatest in soybeans and cotton. There are however, dozens of additional crops that suffer from nematode infestation including potato, pepper, onion, citrus, coffee, sugarcane, greenhouse ornamentals and golf course turf grasses.

Nematode parasites of vertebrates (e.g., humans, livestock and companion animals) include gut roundworms, hookworms, pinworms, whipworms, and filarial worms. They can be transmitted in a variety of ways, including by water contamination, skin penetration, biting insects, or by ingestion of contaminated food.

In domesticated animals, nematode control or "de-worming" is essential to the economic viability of livestock producers and is a necessary part of veterinary care of companion animals. Parasitic nematodes cause mortality in animals (e.g., heartworm in dogs and cats) and morbidity as a result of the parasites inhibiting the ability of the infected animal to absorb nutrients. The parasite-induced nutrient deficiency results in diseased livestock and companion animals (i.e., pets), as well as in stunted growth. For instance, in cattle and dairy herds, a single untreated infection with the brown stomach worm can permanently stunt an animal's ability to effectively convert feed into muscle mass or milk.

Two factors contribute to the need for novel anthelmintics and vaccines for control of parasitic nematodes of animals. First, some of the more prevalent species of parasitic nematodes of livestock are building resistance to the anthelmintic drugs available currently, meaning that these products will eventually lose their efficacy. These developments are not surprising because few effective anthelmintic drugs are available and most have been used continuously. Presently a number of parasitic species has developed resistance to most of the anthelmintics (Geents et al. (1997) Parasitology Today 13:149–151; Prichard (1994) Veterinary Parasitology 54:259–268). The fact that many of the anthelmintic drugs have similar modes of action complicates matters, as the loss of sensitivity of the parasite to one drug is often accompanied by side resistance—that is, resistance to other drugs in the same class (Sangster & Gill (1999) Parasitology Today Vol. 15(4):141–146). Secondly, there are some issues with toxicity for the major compounds currently available.

Human infections by nematodes result in significant mortality and morbidity, especially in tropical regions of Africa, Asia, and the Americas. The World Health Organization estimates 2.9 billion people are infected with parasitic nematodes. While mortality is rare in proportion to total infections (180,000 deaths annually), morbidity is tremendous and rivals tuberculosis and malaria in disability adjusted life year measurements. Examples of human parasitic nematodes include hookworm, filarial worms, and pinworms. Hookworm is the major cause of anemia in millions of children, resulting in growth retardation and impaired cognitive development. Filarial worm species invade the lymphatics, resulting in permanently swollen and deformed limbs (elephantiasis) and invade the eyes causing African Riverblindness. *Ascaris lumbricoides*, the large gut roundworm infects more than one billion people worldwide and causes malnutrition and obstructive bowl disease. In developed countries, pinworms are common and often transmitted through children in daycare.

Even in asymptomatic parasitic infections, nematodes can still deprive the host of valuable nutrients and increase the ability of other organisms to establish secondary infections. In some cases, infections can cause debilitating illnesses and can result in anemia, diarrhea, dehydration, loss of appetite, or death.

While public health measures have nearly eliminated one tropical nematode (the water-borne Guinea worm), cases of other worm infections have actually increased in recent decades. In these cases, drug intervention provided through foreign donations or purchased by those who can afford it remains the major means of control. Because of the high rates of reinfection after drug therapy, vaccines remain the best hope for worm control in humans. There are currently no vaccines available.

Until safe and effective vaccines are discovered to prevent parasitic nematode infections, anthelmintic drugs will continue to be used to control and treat nematode parasitic infections in both humans and domestic animals. Finding effective compounds against parasitic nematodes has been complicated by the fact that the parasites have not been amenable to culturing in the laboratory. Parasitic nematodes are often obligate parasites (i.e., they can only survive in their respective hosts, such as in plants, animals, and/or humans) with slow generation times. Thus, they are difficult to grow under artificial conditions, making genetic and molecular experimentation difficult or impossible. To circumvent these limitations, scientists have used *Caenorhabidits elegans* as a model system for parasitic nematode discovery efforts.

*C. elegans* is a small free-living bacteriovorous nematode that for many years has served as an important model system for multicellular animals (Burglin (1998) *Int. J. Parasitol.*, 28(3): 395–411). The genome of *C. elegans* has been completely sequenced and the nematode shares many general developmental and basic cellular processes with vertebrates (Ruvkin et al. (1998) *Science* 282: 2033–41). This, together with its short generation time and ease of culturing, has made it a model system of choice for higher eukaryotes (Aboobaker et al. (2000) *Ann. Med.* 32: 23–30).

Although *C. elegans* serves as a good model system for vertebrates, it is an even better model for study of parasitic nematodes, as *C. elegans* and other nematodes share unique biological processes not found in vertebrates. For example, unlike vertebrates, nematodes produce and use chitin, have gap junctions comprised of innexin rather than connexin and contain glutamate-gated chloride channels rather than glycine-gated chloride channels (Bargmann (1998) *Science* 282: 2028–33). The latter property is of particular relevance given that the avermectin class of drugs is thought to act at glutamate-gated chloride receptors and is highly selective for invertebrates (Martin (1997) *Vet. J.* 154:11–34).

A subset of the genes involved in nematode specific processes will be conserved in nematodes and absent or significantly diverged from homologues in other phyla. In other words, it is expected that at least some of the genes associated with functions unique to nematodes will have restricted phylogenetic distributions. The completion of the *C. elegans* genome project and the growing database of expressed sequence tags (ESTs) from numerous nematodes facilitate identification of these "nematode specific" genes. In addition, conserved genes involved in nematode-specific processes are expected to retain the same or very similar functions in different nematodes. This functional equivalence has been demonstrated in some cases by transforming *C. elegans* with homologous genes from other nematodes (Kwa et al. (1995) *J. Mol. Biol.* 246:500–10; Redmond et al. (2001) *Mol. Biochem. Parasitol.* 12:125–131). This sort of data transfer has been shown in cross phyla comparisons for conserved genes and is expected to be more robust among species within a phylum. Consequently, *C. elegans* and other free-living nematode species are likely excellent surrogates for parasitic nematodes with respect to conserved nematode processes.

Many expressed genes in *C. elegans* and certain genes in other free-living nematodes can be "knocked out" genetically by a process referred to as RNA interference (RNAi), a technique that provides a powerful experimental tool for the study of gene function in nematodes (Fire et al. (1998) *Nature* 391(6669):806–811; Montgomery et al. (1998) *Proc. Natl. Acad Sci USA* 95(26):15502–15507). Treatment of a nematode with double-stranded RNA of a selected gene can destroy expressed sequences corresponding to the selected gene thus reducing expression of the corresponding protein. By preventing the translation of specific proteins, their functional significance and essentiality to the nematode can be assessed. Determination of essential genes and their corresponding proteins using *C. elegans* as a model system will assist in the rational design of anti-parasitic nematode control products.

SUMMARY

The invention features nucleic acid molecules encoding *M. incognita* phosphoglycerate mutase (PGM) and other nematode PGM-like polypeptides. *M. incognita* is a root knot nematode that causes substantial damage to crops, particularly to cotton, tobacco, pepper, and tomato. PGM-like nucleic acids and polypeptides are useful for the detection of various nematode species and for the identification of compounds that bind to or alter the activity or expression of PGM-like polypeptides. Such compounds may provide a means of combating diseases and infestations caused by nematodes, particularly by *M. incognita*, e.g., in tobacco, cotton, pepper, or tomato plants.

The invention is based, in part, on the identification of a cDNA encoding *M. incognita* PGM (SEQ ID NO: 1). This 1719 nucleotide cDNA has a 1578 nucleotide open reading frame (SEQ ID NO: 3) encoding a 526 amino acid polypeptide (SEQ ID NO: 2).

In one aspect, the invention features novel nematode phosphoglycerate mutase (PGM)-like polypeptides. Such polypeptides include purified polypeptides having the amino acid sequences set forth in SEQ ID NO: 2. Also included are polypeptides having an amino acid sequence that is at least about 68%, 70%, 75%, 80%, 85%, 90%, 95%, or 98% identical to SEQ ID NO: 2. The purified polypeptide can be encoded by a nematode gene, e.g., a nematode other than *C. elegans*. For example, the purified polypeptide has a sequence other than SEQ ID NO: 4 (*C. elegans* PGM). The purified polypeptides can further include a heterologous amino acid sequence, e.g., an amino-terminal or carboxy-terminal sequence. Also featured are purified polypeptide fragments comprising, consisting of, or consisting essentially of, the aforementioned PGM-like polypeptides, e.g., a fragment of at least about 20, 30, 40, 50, 75, 100, 102, 150, 177, 179,183, 185, 200, 250, 300, 350, 400, 450, 500, or 520 amino acids and polypeptides comprising, consisting of, or consisting essentially of such polypeptides. Non-limiting examples of such fragments include: fragments from about amino acid 1 to 120, 1 to 166, 61 to 180, 121 to 240, 166 to 526, 181 to 300, 241 to 360, 301 to 420,361 to 480,421 to 526, and 508 to 526 of SEQ ID NO: 2. Also featured are purified polypeptide subdomains and/or domains of the aforementioned PGM-like polypeptides. Non-limiting examples of such subdomains and/or domains include: Lys3 to Ala75, Val317 to Glu523, and Ile83 to Pro306. The polypeptide or fragment thereof can be modified, e.g., processed, truncated, modified (e.g. by glycosylation, phosphorylation, acetylation, myristylation, prenylation, palmitoylation, amidation, addition of glycerophosphatidyl inositol), or any combination of the above. In certain embodiments the PGM-like polypeptide catalyzes the interconversion of 2- and 3-phosphoglycerates.

Certain PGM-like polypeptides comprise sequences of 535 amino acids or fewer.

In another aspect, the invention features novel isolated nucleic acid molecules encoding a nematode PGM-like polypeptide. Such isolated nucleic acid molecules include nucleic acids having the nucleotide sequence set forth in SEQ ID NO: 1 or SEQ ID NO: 3. Also included are isolated nucleic acid molecules having the same sequence as or encoding the same polypeptide as a nematode PGM-like gene (other than the *C. elegans* PGM-like gene).

Also featured are: 1) isolated nucleic acid molecules having a strand that hybridizes under low stringency conditions to a single stranded probe of the sequence of SEQ ID NO: 3 or its complement and, optionally, encodes a polypeptide of between 465 and 535 (preferably 520 and 530) amino acids; 2) isolated nucleic acid molecules having a strand that hybridizes under high stringency conditions to a single stranded probe of the sequence of SEQ ID NO: 3 or its complement and, optionally, encodes a polypeptide of between 465 and 535 (preferably 520 and 530) amino acids; 3) isolated nucleic acid fragments of PGM-like nucleic acid molecule, e.g., a fragment of SEQ ID NO:1 that is about 100, 200, 300, 400, 500, 555, 560, 575, 750, 1000, 1300, 1500, 1719, or more nucleotides in length or ranges between such lengths; and 4) oligonucleotides that are complementary to a PGM-like nucleic acid molecule or a PGM-like nucleic acid complement, e.g., an oligonucleotide of about 10, 15, 18, 20, 22, 24, 28, 30, 35, 40, 50, 60, 70, 80, or more nucleotides in length. Exemplary oligonucleotides are oligonucleotides which anneal to a site located between nucleotides about 1 to 24, 1 to 48, 1 to 60, 1 to 120, 24 to 48, 24 to 60, 49 to 60, 61 to 180, 1441 to 1560, 1501 to 1620, 1561 to 1680, or 1621 to 1719 of SEQ ID NO: 1. Nucleic acid fragments include the following non-limiting examples: nucleotides about 1 to 500, 149 to 810, 149 to 1000, 559 to 1100, 965 to 1535, 1001 to 1500, and 1501 to 1719 of SEQ ID NO: 1. The isolated nucleic acid can further include a heterologous promoter operably linked to the PGM-like nucleic acid molecule.

A molecule featured herein can be from a nematode of the class Araeolaimida, Ascaridida, Chromadorida, Desmodorida, Diplogasterida, Monhysterida, Mononchida, Oxyurida, Rhigonematida, Spirurida, Enoplia, Desmoscolecidae, or Tylenchida Alternatively, the molecule can be from a species of the class Rhabditida, particularly a species other than C. elegans.

In another aspect, the invention features a vector, e.g., a vector containing an aforementioned nucleic acid. The vector can further include one or more regulatory elements, e.g., a heterologous promoter. The regulatory elements can be operably linked to the PGM-like nucleic acid molecules in order to express a PGM-like nucleic acid molecule. In yet another aspect, the invention features a transgenic cell or transgenic organism having in its genome a transgene containing an aforementioned PGM-like nucleic acid molecule and a heterologous nucleic acid, e.g., a heterologous promoter.

In still another aspect, the invention features an antibody, e.g., an antibody, fragment, or derivative thereof that binds specifically to an aforementioned polypeptide, e.g., a polypeptide consisting of the amino acid sequence of SEQ ID NO: 2. The specificity of the antibody can be such that it does not bind to a C. elegans PGM-like polypeptide. Such antibodies can be polyclonal or monoclonal antibodies. The antibodies can be modified, e.g., humanized, rearranged as a single-chain, or CDR-grafted. The antibodies may be directed against a fragment, a peptide, or a discontinuous epitope from a PGM-like polypeptide.

In another aspect, the invention features a method of screening for a compound that binds to a nematode PGM-like polypeptide, e.g., an aforementioned polypeptide. The method includes providing the nematode polypeptide; contacting a test compound to the polypeptide; and detecting binding of the test compound to the nematode polypeptide. In one embodiment, the method further includes contacting the test compound to a plant or mammalian PGM-like polypeptide; and detecting binding of the test compound to the plant or mammalian PGM-like polypeptide. Preferred compounds are those that bind to a nematode PGM-like polypeptide, but do not substantially bind to at least one selected plant or mammalian PGM-like polypeptide, e.g., do not bind to at least one of cotton, tobacco, pepper, or tomato PGM-like polypeptide. A test compound that binds the nematode PGM-like polypeptide with at least 2-fold, 5-fold, 10-fold, 20-fold, 50-fold, or 100-fold affinity relative to its affinity for the plant or mammalian PGM-like polypeptide can be identified. In another embodiment, the method further includes contacting the test compound to the nematode PGM-like polypeptide and detecting or measuring a PGM-like activity. A decrease in the level of PGM-like activity of the polypeptide relative to the level of PGM-like activity of the polypeptide in the absence of the test compound is an indication that the test compound is an inhibitor of the PGM-like activity. Such inhibitory compounds are potential selective agents for reducing the viability of a nematode expressing a PGM-like polypeptide, e.g., M. incognita.

Another featured method is a method of screening for a compound that alters an activity of a PGM-like polypeptide. The method includes providing the polypeptide; contacting a test compound to the polypeptide and detecting a PGM-like activity, wherein a change in PGM-like activity relative to the PGM-like activity of the polypeptide in the absence of the test compound is an indication that the test compound alters the activity of the polypeptide. The method can further include contacting the test compound to a plant or mammalian PGM-like polypeptide and measuring the PGM-like activity of the plant or mammalian PGM-like polypeptide. A test compound that alters the activity of the nematode PGM-like polypeptide at a given concentration and that does not substantially alter the activity of the plant or mammalian PGM-like polypeptide at the given concentration can be identified. An additional method includes screening for both binding to a PGM-like polypeptide and for alteration in activity of a PGM-like polypeptide.

Yet another featured method is a method of screening for a compound that alters the viability or fitness of a transgenic cell or organism. The transgenic cell or organism has a transgene that expresses a PGM-like polypeptide. The method includes contacting a test compound to the transgenic cell or organism; and detecting the viability or fitness of the transgenic cell or organism.

Also featured is a method of screening for a compound that alters the expression of a nematode nucleic acid encoding a PGM-like polypeptide, e.g. a nucleic acid encoding a M. incognita PGM-like polypeptide. The method includes contacting a cell, e.g., a nematode cell, with a test compound and detecting expression of a nematode nucleic acid encoding a PGM-like polypeptide, e.g., by hybridization to a probe complementary to the nematode nucleic acid encoding an PGM-like polypeptide. Compounds identified by the method are also within the scope of the invention.

In yet another aspect, the invention features a method of treating a disorder caused by a nematode, e.g., M. incognita, in a subject, e.g., a host plant or host animal. The method includes administering to the subject an effective amount of an inhibitor of a PGM-like polypeptide activity or an inhibitor of expression of a PGM-like polypeptide. Non-limiting examples of such inhibitors include: an antisense nucleic acid (or PNA) to a PGM-like nucleic acid, an antibody to a PGM-like polypeptide, or a small molecule identified as a PGM-like polypeptide inhibitor by a method described herein.

A "purified polypeptide", as used herein, refers to a polypeptide that has been separated from other proteins, lipids, and nucleic acids with which it is naturally associated. The polypeptide can constitute at least about 10, 20, 50, 70, 80 or 95% by dry weight of the purified preparation.

An "isolated nucleic acid" is a nucleic acid, the structure of which is not identical to that of any naturally occurring nucleic acid, or to that of any fragment of a naturally occurring genomic nucleic acid spanning more than three separate genes. The term therefore covers, for example, (a) a DNA which is part of a naturally occurring genomic DNA molecule but is not flanked by both of the nucleic acids that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones: e.g., as these occur in a DNA library such as a cDNA or genomic DNA library. Isolated nucleic acid molecules according to the present invention further include molecules produced synthetically, as well as any nucleic acids that have been altered chemically and/or that have modified backbones.

Although the phrase "nucleic acid molecule" primarily refers to the physical nucleic acid molecule and the phrase "nucleic acid sequence" refers to the sequence of the nucleotides in the nucleic acid molecule, the two phrases can be used interchangeably.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

The "percent identity" of two amino acid sequences or of two nucleic acids is determined using the algorithm of Karlin and Altschul (1990) Proc. Natl. Acad. Sci. USA 87:2264–68, 1990, modified as in Karlin and Altschul (1993) Proc. Natl. Acad. Sci. USA 90:5873–77, 1993. Such an algorithm is incorporated into the BLASTN and BLASTX programs (version 2.0) of Altschul et al. (1990) J. Mol. Biol. 215:403–10. BLAST nucleotide searches can be performed with the BLASTN program, score=100, wordlength=12 to obtain nucleotide sequences homologous to the nucleic acid molecules of the invention. BLAST protein searches can be performed with the BLASTX program, score=50, wordlength=3 to obtain amino acid sequences homologous to the protein molecules of the invention. Where gaps exist between two sequences, Gapped BLAST can be utilized as described in Altschul (1997) et al., Nucleic Acids Res. 25:3389–3402. When utilizing BLAST and Gapped BLAST programs, the default parameters of the respective programs (e.g., BLASTX and BLASTN) can be used. See http://www.ncbi.nlm.nih.gov.

As used herein, the term "transgene" means a nucleic acid sequence (encoding, e.g., one or more subject polypeptides), which is partly or entirely heterologous, i.e., foreign, to the transgenic plant or cell into which it is introduced, or, is homologous to an endogenous gene of the transgenic plant or cell into which it is introduced, but which is designed to be inserted, or is inserted, into the plant's genome in such a way as to alter the genome of the cell into which it is inserted (e.g., it is inserted at a location which differs from that of the natural gene or its insertion results in a knockout). A transgene can include one or more transcriptional regulatory sequences and other nucleic acid sequences, such as introns, that may be necessary for optimal expression of the selected nucleic acid, all operably linked to the selected nucleic acid, and may include an enhancer sequence.

As used herein, the term "transgenic cell" refers to a cell containing a transgene.

As used herein, a "transgenic plant" is any plant in which one or more, or all, of the cells of the plant includes a transgene. The transgene can be introduced into the cell, directly or indirectly by introduction into a precursor of the cell, by way of deliberate genetic manipulation, such as by T-DNA mediated transfer, electroporation, or protoplast transformation. The transgene may be integrated within a chromosome, or it may be extrachromosomally replicating DNA.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as a leaf, a root, or a stem.

As used herein, the terms "hybridizes under stringent conditions" and "hybridizes under high stringency conditions" refers to conditions for hybridization in 6×sodium chloride/sodium citrate (SSC) at about 45° C., followed by two washes in 0.2×SSC, 0.1% SDS at 65° C. As used herein, the term "hybridizes under low stringency conditions" refers to conditions for hybridization in 6×sodium chloride/sodium citrate (SSC) at about 45° C., followed by two washes in 6×SSC buffer, 0.1% (w/v) SDS at 50° C.

A "heterologous promoter", when operably linked to a nucleic acid sequence, refers to a promoter which is not naturally associated with the nucleic acid sequence.

As used herein, an agent with "antihelminthic activity" is an agent, which when tested, has measurable nematode-killing activity or results in infertility or sterility in the nematodes such that unviable or no offspring result. In the assay, the agent is combined with nematodes, e.g., in a well of microtiter dish having agar media or in the soil containing the agent. Staged adult nematodes are placed on the media. The time of survival, viability of offspring, and/or the movement of the nematodes are measured. An agent with "antihelminthic activity" reduces the survival time of adult nematodes relative to unexposed similarly-staged adults, e.g., by about 20%, 40%, 60%, 80%, or more. In the alternative, an agent with "antihelminthic activity" may also cause the nematodes to cease replicating, regenerating, and/or producing viable progeny, e.g., by about 20%, 40%, 60%, 80%, or more.

As used herein, the term "binding" refers to the ability of a first compound and a second compound that are not covalently attached to physically interact. The apparent dissociation constant for a binding event can be 1 mM or less, for example, 10 nM, 1 nM, 0.1 nM or less.

As used herein, the term "binds specifically" refers to the ability of an antibody to discriminate between a target ligand and a non-target ligand such that the antibody binds to the target ligand and not to the non-target ligand when simultaneously exposed to both the target ligand and non-target ligand, and when the target ligand and the non-target ligand are both present in a molar excess over the antibody.

A used herein, the term "altering an activity" refers to a change in level, either an increase or a decrease in the activity, particularly a PGM-like or PGM activity. The change can be detected in a qualitative or quantitative observation. If a quantitative observation is made, and if a comprehensive analysis is performed over a plurality of observations, one skilled in the art can apply routine statistical analysis to identify modulations where a level is changed and where the statistical parameter, the p value, is less than 0.05.

In part, the nematode PGM proteins and nucleic acids described herein are novel targets for anti-nematode vaccines, pesticides, and drugs. Inhibition of these molecules can provide means of inhibiting nematode metabolism and/or the nematode life-cycle.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A–1B depict *M. incognita* PGM-like nucleic acid sequence (SEQ ID NO: 1), and its corresponding encoded amino acid sequence (SEQ ID NO: 2). The open-reading fame of SEQ ID NO: 1 extends for nucleotide 22 to 1599 of SEQ ID NO: 1 (SEQ ID NO: 3).

FIGS. 2A–2B depict the amino acid sequence of *C. elegans* phosphoglycerate mutates (SEQ ID NO: 4; GenBank nr Accession No. F57B10.3).

FIG. 3 depicts an alignment of the amino acid sequences of *M. incognita* (SEQ ID NO: 2) PGM-like polypeptide and *C. elegans* phosphoglycerate mutates (SEQ ID NO: 4; GenBank nr Accession No. F57B10.3).

DETAILED DESCRIPTION

Phosphoglycerate mutase (PGM) is an enzyme of the glycolytic and gluconeogenic pathways that catalyzes the interconversion of 3-phospho-D-glycerate [3-PGA] and 2-phospho-D-glycerate [2-PGA] in the Embden-Meyerhoff pathway. Two apparently evolutionary unrelated PGM enzymes have been characterized which are both kinetically and structurally distinct The two different PGM enzymes can be distinguished most readily by the dependence of one on 2,3-biphophoglycerate as a cofactor (dPGM) and co-factor-independence of the other (iPGM). Accordingly, dPGM catalyzes the intermolecular transfer of phospho groups between the substrate and the co-factor. In contrast, iPGM catalyzes the intramolecular transfer of phospho groups (Forthergill-Gilmore et al. (1989) *Adv. Enzymology*. 62, 227–313; Fothergill-Gilmore et al. (1993) *Prog. Biophys. Mol. Biol.* 59: 105–235).

Co-factor-dependent mutases from a variety of organisms have been extensively characterized by sequencing of genes, analysis of enzyme kinetics, mutagenesis experiments and crystallography. Based on these studies, it has been determined that the dPGMs are active as monomers, dimers, or tetramers depending upon the organism from which the enzymes have been isolated (Rigden et al. (1998) *J. Mol. Biol.* 2:449459). iPGMs remain less well characterized, but are known to be monomers in solution and show no apparent sequence homology with those of the dPGM family. In addition, it is known that iPGMs are members of the alkaline phosphatase superfamily, a family composed of a wide range of enzymes catalyzing the transfer of phospho- or sulfate groups (e.g., phosphopentomutase, phosphoglycerol transferase, $Ca^{2+}$-dependent ATPase and a number of sulphatases). These enzymes share a very limited degree of sequence identity that may reflect conservation of certain active site and metal binding residues (Galperin et al. (1998) *Protein Sci.* 7:1829–1835). Details of the catalytic mechanism of iPGM are not well understood, though a phosphoenzyme intermediate has been postulated and essential histidine residues have been identified.

The distribution of PGMs in various organisms is complex and difficult to explain. Vertebrates, budding yeast, and some eubacterial species have only dPGM while nematodes, archea, higher plants and other eubacteria possess only iPGM. The distribution in bacteria is remarkable, as it appears that organisms with larger genomes, such as *E. coli, B. subtilis*, and *Synechocystis sp.* have genes coding for both classes of the enzyme, while organisms with smaller genomes encode for only one of the enzymes. For example, iPGM is the only form of this enzyme that is encoded in the genomes of such human pathogens as *Mycoplasma genitalium, Mycoplasma pneumoniae*, and *Helicobacter pylor* (Galperin et al. (1998) *Protein Sci.* 7:1829–1835; Fraser et al. (1999) *FEBS Letters*, 455:344–348).

Genetic and bioinformatic studies have revealed a complex phylogenetic distribution even within the iPGM group with several clusters of enzymes present. For example, the iPGM enzymes present in nematodes are more closely related to enzymes present in some types of bacteria than to the co-factor independent enzymes present in plants. Thus, the iPGMs present in parasitic nematodes are not only phylogenetically distinct from the dPGMs of vertebrates but also significantly diverged from homologs identified in plants. The complex distribution of PGM enzymes in a variety of organisms makes the PGM of parasitic nematodes a suitable drug or pesticide target, because it should be possible to identify inhibitors selective for a nematode PGM.

Compounds that inhibit glycolysis can be toxic to nematodes (Butterworth et al. (1989) *Revue de Nematologie* 12:63–67). The phosphoglycerate mutase class of enzymes include enzymes that are fundamental to glycolysis and gluconeogenesis. Thus, PGM is an attractive target for the development of compounds toxic to nematodes.

The present invention provides nucleic acids from nematodes encoding PGM-like polypeptides. The nucleotide sequence and encoded amino acid sequence of *M. incognita* PGM are recited in FIGS. 1A–1B. The present invention is based, in part, on the discovery of these PGM-like sequences from *M. incognita*. The following example is, therefore, to be construed as merely illustrative, and not limiting. All of the publications cited herein are hereby incorporated by reference in their entirety.

EXAMPLE

TBLASTN searches of publicly available sequence databases identified several expressed sequence tags (ESTs; short nucleic acid fragment sequences from single sequencing reads) that are similar to a PGM-like *C. elegans* gene (GenBank nr accession number F57B10.3; GenBank NM_059495). A query with *C. elegans* PGM-like sequence identified ESTs in four nematode species: (AW783013 from *M. incognita*; McCarter et al., (1999) Washington University Nematode EST Project); AW152739 (from *Litomosoides sigmodontis*; Allen et al. (2000) Infect. Immun. 68: 5454–8 2000) similar to *C. elegans* PGM codons 278–493; and BF423140 (from *Haemonchus contortus*; Blaxter et al.

(2000) Edinburgh University/Sanger Centre Nematode EST Project) similar to *C. elegans* PGM codons 31–197; and AW499468 (from *Onchocerca volvulus*; Williams et al. (1999) Benhard Nocht Institute for Tropical Medicine, Hamburg, Germany) similar to *C. elegans* PGM codons 25–173.

Full Length PGM-like cDNA Sequences

A full length (containing the complete open reading frame) DNA sequence for the *C. elegans* PGM was generated computationally from raw cosmid sequence data present in the GenBank nr database. Hypothetical exon sequences were spliced together manually by removing intervening intron sequences such that the final cDNA sequence, when conceptually translated, exactly matched the predicted protein sequences for the *C. elegans* PGM sequence reported in the GenBank nr database.

Plasmid clone, Div114, corresponding to the *M. incognita* EST sequence (AW783013) was obtained from the Genome Sequencing Center (St. Louis, Mo.). The cDNA insert in the plasmid was sequenced in its entirety. Unless otherwise indicated, all nucleotide sequences determined herein were sequenced with an automated DNA sequencer (such as model 373 from Applied Biosystems, Inc.) using processes well-known to those skilled in the art. Primers used for sequencing are listed in Table 1 (see below).

TABLE 1

| Name | Sequence | Homology to |
|---|---|---|
| T7 | gta ata cga ctc act ata ggg c (SEQ ID NO: 5) | vector polylinker primer |
| T3 | aat taa ccc tca cta aag gg (SEQ ID NO: 6) | vector polylinker primer |
| Oligo dT | gag aga gag aga gag aga gaa cta gtc tcg agt ttt ttt ttt ttt tt (SEQ ID NO: 7) | Universal primer to poly A tail |
| SL1 | ggg ttt aat tac cca agt ttg a (SEQ ID NO: 8) | Nematode transpliced leader |
| Pgm1 | gag act gac gaa ttt ctg (SEQ ID NO: 9) | Mi PGM (codons 234–239) |
| Pgm2 | cag aaa ttc gtc agt ctc (SEQ ID NO: 10) | Mi PGM (codons 234–239) |
| Pgm5 | gtt att gat gga tgg gg (SEQ ID NO: 11) | Mi PGM (codons 15–20) |
| Pgm5 (comp) | ccc cat cca tca ata ac (SEQ ID NO: 12) | Mi PGM (codons 15–20) |
| Pgm6 | cca gaa ggc tta atg gga aa (SEQ ID NO: 13) | Mi PGM (codons 59–65) |
| Pgm6 (comp) | ttt ccc att aag cct tct gg (SEQ ID NO: 14) | Mi PGM (codons 59–65) |

Partial sequence data for the *M. incognita* PGM was obtained from Div114, including nucleotide sequence for codons 148–526 and additional 3' untranslated sequence. The clone lacked the amino terminus of the *M. incognita* PGM as well as the 5' untranslated region.

The following methods were used to obtain the full-length *M. incognita* PGM-like gene and to determine its complete sequence.

First, RNA was obtained from *M. incognita*, which were maintained on greenhouse pot cultures of Rutgers tomato (Burpee). Total RNA was isolated using the TRIZOL reagent (Gibco BRL). Briefly, 2 ml of packed worms were combined with 8 ml TRIZOL reagent and solubilized by vortexing. Following 5 minutes of incubation at room temperature, the samples were spun at 14,000×g for 10 minutes at 4° C. to remove insoluble material. The liquid phase was extracted with 200 µl of chloroform, and the upper aqueous phase was removed to a fresh tube. The RNA was precipitated by the addition of 500 µl of isopropanol and centrifuged to pellet. The aqueous phase was carefully removed, and the pellet was washed in 75% ethanol and spun to re-collect the RNA pellet. The supernatant was carefully removed, and the pellet was air dried for 10 minutes. The RNA pellet was resuspended in 50 µl of DEPC-$H_2O$ and analyzed by spectrophotometry at 260 nm and 280 nm to determine yield and purity.

To obtain the missing 5' sequence of the *M. incognita* PGM gene, 5' RACE technique was applied, and SL1 PCR was performed using first strand cDNA from *M. incognita* as a template. Briefly, SL1 PCR utilizes the observation, that unlike most eukaryotic mRNAs, many nematode MRNA molecules contain a common leader sequence (5' ggg ttt aat tac cca agt ttg a 3') transpliced to their 5' ends. If this sequence is present on the 5' end of a cDNA, that cDNA can be amplified using PCR with a primer that binds to the SL1 transpliced leader and a gene-specific primer near the 3' end of the cDNA.

Briefly, following the instructions provided by Life Technologies CDNA synthesis kit, first strand cDNA synthesis was performed on total nematode RNA using SuperScript™ II Reverse Transcriptase and an oligo-dT primer (which anneals to the natural poly A tail found on the 3' end of all eukaryotic mRNA). RNase H was then used to degrade the original m RNA template. Following degradation of the original mRNA template, the first strand cDNA was directly PCR amplified without further purification using Taq DNA polymerase, a gene specific primer designed from known sequence that anneals to a site located within the first strand cDNA molecule, and the SL1 primer, which is homologous the 5' end of the the cDNA of interest. Amplified PCR products were then cloned into a suitable vector for DNA sequence analysis. This procedure was performed to obtain clones Div234 and Div235. These clones contained codons 1–239 in addition to 5' untranslated sequences. Taken together, clones Div114, Div234, and Div235 contain sequences comprising the complete open reading frame of the PGM gene from *M. incognita*. The assigned open-reading frame is shown in FIGS. 1A–1B.

Characterization of *M. incognita* PGM

The sequence of the *M. incognita* PGM-like nucleic acid molecule is recited in FIGS. 1A–1B as SEQ ID NO: 1. This nucleotide sequence contains an open reading frame (SEQ ID NO: 3) encoding a 526 amino acid polypeptide (FIGS. 1A–1B; SEQ ID NO: 2). The *M. incognita* PGM-like protein is approximately 66% identical to the *C. elegans* PGM gene (depicted in FIGS. 2A–2B as SEQ ID NO: 4).

The similarity between the *M. incognita* PGM-like protein sequences and other sequences was investigated by comparison to the sequences of other nematodes genes, e.g., *C. elegans*. The similarity between PGM-like protein sequences from *M. incognita* and from *C. elegans* is presented as a multiple alignment generated by the ClustalX multiple alignment program as described below (FIG. 3).

The similarity between *M. incognita* PGM sequence and other sequences was also investigated by comparison to sequence databases using BLASTP analysis against nr (a non-redundant sequence database available on the World Wide Web at www.ncbi.nlm.nih.gov) and TBLASTN analysis against dbest (an EST sequence database available on the World Wide Web at www.ncbi.nlm.nih.gov; top 500 hits; E=1e-4). The "Expect (E) value" is the number of sequences that are predicted to align by chance given the size of the queried database. This analysis was used to determine the potential number of plant and vertebrate homologs. Neither C. elegans nor Meloidogyne PGM-like sequences had vertebrate hits in nr or dbest having sufficient sequence similarity to meet the threshold E value of 1e4 (this E value approximately corresponds to a threshold for removing sequences having a sequence identity of less than about 20% over greater than 50 amino acids). Thus, the *M. incognita* PGM-like enzymes of this invention do not appear to share significant sequence similarity with the more common vertebrate forms of the enzyme such as the *Homo sapiens* phosphoglycerate gene P40926. The analysis also determined that there were PGM-like sequences with plant hits in nr and dbest. It is known, however, that PGM-like enzymes present in nematodes are more closely related to enzymes present in some types of bacteria than to the co-factor independent enzymes present in plants. Thus, the PGM-like enzymes present in nematodes are not only phylogenetically distinct from the PGM-like enzymes of vertebrates but also significantly diverged from homologs identified in plants. On the basis of the lack of similarity, the *M. incognita* PGM-like enzymes are useful targets of inhibitory compounds selective for nematodes over their hosts (e.g., humans, animals, and plants).

Functional predictions were made with PFAM (available on the Internet at pfam.wustl.edu/), which is a Hidden Markov Model based database of families of protein domains. No hits were found in searches using either the *C. elegans* or *M. incognita* polypeptides as queries suggesting that these polypeptides are a novel class of PGM-like enzymes. Protein localization was predicted using the TargetP server (available on the Internet at cbs.dtu.dk/services/TargetP). The *C. elegans* PGM was predicted to be mitochondrial and the *M. incognita* PGM was predicted to be cytosolic.

Identification of Additional PGM-like Sequences

A skilled artisan can utilize the methods provided in the example above to identify additional nematode PGM-like sequences, e.g., PGM-like sequence from nematodes other than *C. elegans* and *M. incognita*. In addition, nematode PGM-like sequences can be identified by a variety of methods including computer-based database searches, hybridization-based methods, and functional complementation.

Database Identification. A nematode PGM-like sequence can be identified from a sequence database, e.g., a protein or nucleic acid database using a sequence disclosed herein as a query. Sequence comparison programs can be used to compare and analyze the nucleotide or amino acid sequences. One such software package is the BLAST suite of programs from the National Center for Biotechnology Institute's (NCBI; Altschul et al. (1997) *Nuc. Acids Research* 25:3389–3402.). A PGM-like sequence of the invention can be used to query a sequence database, such as nr, nemnoele (a database of nematode sequences extracted from dbest and lacking *C. elegans* sequences), dbest (expressed sequence tag (EST) sequences), and htgs (high-throughput genome sequences), using a computer-based search, e.g., FASTA, BLAST, or PSI-BLAST search. Homologous sequences in other species (e.g., humans, plants, animals, fungi) can be detected in a PSI-BLAST search of a database such as nr (E value=1e-2, H value=1e-4, using, for example, four iterations; http://www.ncbi.nlm.nih.gov/). Sequences so obtained can be used to construct a multiple alignment, e.g., a ClustalX alignment, and/or to build a phylogenetic tree, e.g., in ClustalX using the Neighbor-Joining method (Saitou and Nei (1987) *Mol. Biol. Evol.* 4:406425) and bootstrapping (1000 replicates; Felsenstein (1985) *Evolution* 39:783–791).

Distances may be corrected for the occurrence of multiple substitutions $[D_{corr} = -\ln(1-D-D^2/5)$ where D is the fraction of amino acid differences between two sequences] (Kimura (1983) *The Neutral Theory of Molecular Evolution*).

The aforementioned search strategy can be used to identify PGM-like sequences in nematodes of the following non-limiting, exemplary genera invention can be used to treat diseases or infestations caused by nematodes of the following non-limiting, exemplary genera:

Plant nematode genera: Afrina, Anguina, Aphelenchoides, Belonolaimus, Bursaphelenchus, Cacopaurus, Cactodera, Criconema, Criconemoides, Cryphodera, Ditylenchus, Dolichodorus, Dorylaimus, Globodera, Helicotylenchus, Hemicriconemoides, Hemicycliophora, Heterodera, Hirschmanniella, Hoplolaimus, Hypsoperine, Longidorus, Meloidogyne, Mesoanguina, Nacobbus, Nacobbodera, Panagrellus, Paratrichodorus, Paratylenchus, Pratylenchus, Pterotylenchus, Punctodera, Radopholus, Rhadinaphelenchus, Rotylenchulus, Rotylenchus, Scutellonema, Subanguina, Thecavermiculatus, Trichodorus, Turbatrix, Tylenchorhynchus, Tylenchulus, Xiphinema Animal and human nematode genera: Acanthocheilonema, Aelurostrongylus, Ancylostoma, Angiostrongylus, Anisakis, Ascaris, Ascarops, Bunostomum, Brugia, Capillaria, Chabertia, Cooperia, Crenosoma, Cyathostome species (Small Strongyles), Dictyocaulus, Dioctophyma, Dipetalonema, Dirofiliaria, Dracunculus, Draschia, Elaneophora, Enterobius, Filaroides, Gnathostoma, Gonylonema, Habronema, Haemonchus, Hyostrongylus, Lagochilascaris, Litomosoides, Loa, Mammomonogamus, Mansonella, Muellerius, Metastrongylid, Necator, Nematodirus, Nippostrongylus, Oesophagostomum, Ollulanus, Onchocerca, Ostertagia, Oxyspirura, Oxyuris, Parafilaria, Parascaris, Parastrongyloides, Parelaphostrongylus, Physaloptera, Physocephalus, Protostrongylus, Pseudoterranova, Setaria, Spirocerca, Stephanurus, Stephanofilaria, Strongyloides, Strongylus, Spirocerca, Syngamus, Teladorsagia, Thelazia, Toxascaris, Toxocara, Trichinella, Trichostrongylus, Trichuris, Uncinaria, and Wuchereria.

Particularly prefeffed nematode genera include: Plant: Anguina, Aphelenchoides, Belonolaimus, Bursaphelenchus, Ditylenchus, Dolichodorus, Globodera, Heterodera, Hoplolaimus, Longidorus, Meloidogyne, Nacobbus, Pratylenchus, Radopholus, Rotylenchus, Tylenchulus, Xiphinema.

Animal and human: Ancylostoma, Ascaris, Brugia, Capillaria, Cooperia, Cyathostome species, Dictyocaulus, Dirofiliaria, Dracunculus, Enterobius, Haemonchus, Necator, Nematodirus, Oesophagostomum, Onchocerca, Ostertagia, Oxyspirura, Oxyuris, Parascaris, Strongyloides, Strongylus, Syngamus, Teladorsagia, Thelazia, Toxocara, Trichinella, Trichostrongylus, Trichuris, and Wuchereria.

Particularly preferred nematode species include: Plant: *Anguina tritici, Aphelenchoides fragariae, Belonolaimus longicaudatus, Bursaphelenchus xylophilus, Ditylenchus destructor, Ditylenchus dipsaci Dolichodorus heterocephalous, Globodera pallida, Globodera rostochiensis, Globodera tabacum, Heterodera avenae, Heterodera cardiolata, Heterodera carotae, Heterodera cruciferae, Heterodera glycines, Heterodera major, Heterodera schachtii, Heterodera zeae, Hoplolaimus tylenchiformis, Longidorus sylphus, Meloidogyne acronea, Meloidogyne arenaria, Meloidogyne chitwoodi, Meloid-* ogyne exigua, Meloidogyne graminicola, Meloidogyne hapla, Meloidogyne incognita, Meloidogyne javanica, Meloidogyne nassi, Nacobbus batatiformis, Pratylenchus brachyurus, Pratylenchus coffeae, Pratylenchus penetrans, Pratylenchus scribneri, Pratylenchus zeae, Radopholus similis, Rotylenchus reniformis, Tylenchulus semipenetrans, Xiphinema americanum.

Animal and human: Ancylostoma braziliense, Ancylostoma caninum, Ancylostoma ceylanicum, Ancylostoma duodenale, Ancylostoma tubaeforme, Ascaris suum, Ascaris lumbrichoides, Brugia malayi, Capillaria bovis, Capillariaplica, Capillariafeliscati, Cooperia oncophora, Cooperia punctata, Cyathostome species, Dictyocaulus filaria, Dictyocaulus viviparus, Dictyocaulus arnfleldi, Dirofiliaria immitis, Dracunculus insignis, Enterobius vermicularis, Haemonchus contortus, Haemonchus placei, Necator americanus, Nematodirus helvetianus, Oesophagostomum radiatum, Onchocerca volvulus, Onchocerca cervicalis, Ostertagia ostertagi, Ostertagia circumcincta, Oxyuris equi, Parascaris equorum, Strongyloides stercoralis, Strongylus vulgaris, Strongylus edentatus, Syngamus trachea, Teladorsagia circumcincta, Toxocara cati, Trichinella spiralis, Trichostrongylus axei, Trichostrongylus colubriformis, Trichuris vulpis, Trichuris suis, Trichurs trichiura, and Wuchereria bancrofti.

Further, a PGM-like sequence can be used to identify additional PGM-like sequence homologs within a genome. Multiple homologous copies of a PGM-like sequence can be present. For example, a nematode PGM-like sequence can be used as a seed sequence in an iterative PSI-BLAST search (default parameters, substitution matrix=Blosum62, gap open=11, gap extend=1) of a database, such as nr or wormpep (E value=1e-2, H value=1e4, using, for example 4 iterations) to determine the number of homologs in a database, e.g., in a database recording the genome of the organism (such as in the completed C. elegans genome). A nematode PGM-like sequence can be present in a genome along with 1, 2, 3, 4, 5, 6, 8, 10, or more homologs.

Hybridization Methods. A nematode PGM-like sequence can be identified by a hybridization-based method using a sequence provided herein as a probe. For example, a library of nematode genomic or cDNA clones can be hybridized under low stringency conditions with the probe nucleic acid. Stringency conditions can be altered to reduce background signal and increase signal from potential positives. Clones so identified can be sequenced to verify that they encode PGM-like sequences.

Another hybridization-based method utilizes an amplification reaction (e.g., the polymerase chain reaction (PCR)). Oligonucleotides, e.g., degenerate oligonucleotides, are designed to hybridize to a conserved region of a PGM-like sequence (e.g., a region conserved in both sequences depicted in FIG. 3). The oligonucleotides are used as primers to amplify a PGM-like sequence from template nucleic acid from a nematode, e.g., a nematode other than C. elegans or M. incognita. The amplified fragment can be cloned and/or sequenced.

Complementation Methods. A nematode PGM-like sequence can be identified from a complementation screen for a nucleic acid molecule that provides a PGM-like activity to a cell lacking a PGM-like activity. Routine methods can be used to construct bacterial or yeast strains that lack, e.g., PGM activity. For example, a Saccharamyces cerevisiae strain deleted for the PGM gene can be isolated (Rodicio et al. (1987) Mol Gen Genet. 206: 133–140 and Heinisch et al. (1998) Yeast 14: 203–213). Such a strain can be transformed with a plasmid library expressing nematode cDNAs. Strains are identified in which PGM activity is restored. For example, the pgmS. cerevisiae strain transformed with the plasmid library can be grown on glucose as the sole source of carbon and energy to select for strains expressing a nematode PGM-like gene. The plasmid harbored by the strain can be recovered to identify and/or characterize the inserted nematode CDNA that provides PGM-like activity when expressed.

Methods for generating full-length cDNA. 5' and 3' RACE techniques can be used in combination with EST sequence information to generate full-length cDNAs. The molecular technique 5' RACE (Life Technologies, Inc., Rockville, Md.) is employed to obtain complete or near-complete 5' ends of CDNA sequences for a nematode PGM-like cDNA sequences. Briefly, following the instructions provided by Life Technologies, first strand CDNA is synthesized from total M. incognita RNA using Murine Leukemia Virus Reverse Transcriptase (M-MLV RT) and a gene specific "antisense" primer, e.g., designed from available EST sequence. RNase H is used to degrade the original mRNA template. The first strand cDNA is separated from unincorporated dNTPs, primers, and proteins using a Glass-MAX Spin Cartridge. Terminal deoxynucleotidyl transferase (TdT) is used to generate a homopolymeric dC tailed extension by the sequential addition of dCTP nucleotides to the 3' end of the first strand cDNA. Following addition of the dC homopolymeric extension, the first strand cDNA is directly amplified without further purification using Taq DNA polymerase, a gene specific "antisense" primer designed from available EST sequences to anneal to a site located within the first strand cDNA molecule, and a deoxyinosine-containing primer that anneals to the homopolymeric dC tailed region of the cDNA in a polymerase chain reaction (PCR). 5' RACE PCR amplification products are cloned into a suitable vector for further analysis and sequenced.

The molecular technique, 3' RACE (Life Technologies, Inc.; Rockville, Md.), is employed to obtain complete or near-complete 3' ends of cDNA sequences for M. incognita PGM-like cDNA sequences. Briefly, following the instructions provided by Life Technologies (Rockville, Md.), first strand cDNA synthesis is performed on total nematode RNA using SuperScript™ Reverse Transcriptase and an oligo-dT primer that anneals to the polyA tail. Following degradation of the original MRNA template with RNase H, the first strand cDNA is directly PCR amplified without further purification using Taq DNA polymerase, a gene specific primer designed from available EST sequences to anneal to a site located within the first strand cDNA molecule, and a "uiversal" primer which contains sequence identity to 5' end of the oligo-dT primer. 3' RACE PCR amplification products are cloned into a suitable vector for further analysis and sequenced.

Nucleic Acid Variants

Isolated nucleic acid molecules of the present invention include nucleic acid molecules that have an open reading frame encoding a PGM-like polypeptide. Such nucleic acid molecules include molecules having: the sequences recited in SEQ ID NO: 1 and sequences coding for the PGM-like protein recited in SEQ ID NO: 2. These nucleic acid molecules can be used, for example, in a hybridization assay to detect the presence of a M. incognita nucleic acid in a sample.

The present invention includes nucleic acid molecules such as those shown in SEQ ID NO: 1 or SEQ ID NO: 3 that may be subjected to mutagenesis to produce single or multiple nucleotide substitutions, deletions, or insertions. Nucleotide insertional derivatives of the nematode gene of the present invention include 5' and 3' terminal fusions as well as intra-sequence insertions of single or multiple nucleotides. Insertional nucleotide sequence variants are those in which one or more nucleotides are introduced into a predetermined site in the nucleotide sequence, although random insertion is also possible with suitable screening of the resulting product. Deletion variants are characterized by the removal of one or more nucleotides from the sequence. Nucleotide substitution variants are those in which at least one nucleotide in the sequence has been removed and a different nucleotide inserted in its place. Such a substitution may be silent (e.g., synonymous), meaning that the substitution does not alter the amino acid defined by the codon. Alternatively, substitutions are designed to alter one amino acid for another amino acid (e.g., non-synonymous). A non-synonymous substitution can be conservative or non-conservative. A substitution can be such that activity, e.g., a phosphoglycerate mutase-like activity, is not impaired. A conservative amino acid substitution results in the alteration of an amino acid for a similar acting amino acid, or amino acid of like charge, polarity, or hydrophobicity, e.g., an amino acid substitution listed in Table 2 below. At some positions, even conservative amino acid substitutions can disrupt the activity of the polypeptide.

TABLE 2

Conservative Amino Acid Replacements

| For Amino | Code | Replace with any of |
|---|---|---|
| Alanine | Ala | Gly, Cys, Ser |
| Arginine | Arg | Lys, His |
| Asparagine | Asn | Asp, Glu, Gln, |
| Aspartic Acid | Asp | Asn, Glu, Gln |
| Cysteine | Cys | Met, Thr |
| Glutamine | Gln | Asn, Glu, Asp |
| Glutamic Acid | Glu | Asp, Asn, Gln |
| Glycine | Gly | Ala |
| Histidine | His | Lys, Arg |
| Isoleucine | Ile | Val, Leu, Met |
| Leucine | Leu | Val, Ile, Met |
| Lysine | Lys | Arg, His |
| Methionine | Met | Ile, Leu, Val |
| Phenylalanine | Phe | Tyr, His, Trp |
| Proline | Pro | |
| Serine | Ser | Thr, Cys, Ala |
| Threonine | Thr | Ser, Met, Val |
| Tryptophan | Trp | Phe, Tyr |
| Tyrosine | Tyr | Phe, His |
| Valine | Val | Leu, Ile, Met |

The current invention also embodies splice variants of nematode PGM-like sequences.

Another aspect of the present invention embodies a polypeptide-encoding nucleic acid molecule that is capable of hybridizing under conditions of low stringency to a nucleic acid molecule having the sequence of SEQ: ID NO: 3, or its complement.

The nucleic acid molecules that encode for PGM-like polypeptides may correspond to the naturally occurring nucleic acid molecules or may differ by one or more nucleotide substitutions, deletions, and/or additions. Thus, the present invention extends to genes and any functional mutants, derivatives, parts, fragments, homologs or analogs thereof or non-functional molecules. Such nucleic acid molecules can be used to detect polymorphisms of PGM genes or PGM-like genes, e.g., in other nematodes. As mentioned below, such molecules are useful as genetic probes; primer sequences in the enzymatic or chemical synthesis of the gene; or in the generation of immunologically interactive recombinant molecules. Using the information provided herein, such as the nucleotide sequence SEQ ID NO: 1 or SEQ ID NO: 3, a nucleic acid molecule encoding a PGM-like molecule may be obtained using standard cloning and a screening techniques, such as a method described herein.

Nucleic acid molecules of the present invention can be in the form of RNA, such as mRNA, or in the form of DNA, including, for example, cDNA and genomic DNA obtained by cloning or produced synthetically. The DNA may be double-stranded or single-stranded The nucleic acids may in the form of RNA/DNA hybrids. Single-stranded DNA or RNA can be the coding strand, also referred to as the sense strand, or the non-coding stand, also known as the anti-sense strand.

One embodiment of the present invention includes a recombinant nucleic acid molecule, which includes at least one isolated nucleic acid molecule depicted in SEQ ID NO: 1 or SEQ ID NO: 3, inserted in a vector capable of delivering and maintaining the nucleic acid molecule into a cell. The DNA molecule may be inserted into an autonomously replicating factor (suitable vectors include, for example, pGEM3Z and pcDNA3, and derivatives thereof). The vector nucleic acid may be a bacteriophage DNA such as bacteriophage lambda or M13 and derivatives thereof. The vector may be either RNA or DNA, single- or double-stranded, prokaryotic, eukaryotic, or viral. Vectors can include transposons, viral vectors, episomes, (e.g. plasmids), chromosomes inserts, and artificial chromosomes (e.g. BACs or YACs). Construction of a vector containing a nucleic acid described herein can be followed by transformation of a host cell such as a bacterium. Suitable bacterial hosts include, but are not limited to, *E. coli*. Suitable eukaryotic hosts include yeast such as *S. cerevisiae*, other fungi, vertebrate cells, invertebrate cells (e.g., insect cells), plant cells, human cells, human tissue cells, and whole eukaryotic organisms. (e.g. a transgenic plant or a transgenic animal). Further, the vector nucleic acid can be used to generate a virus such as vaccinia or baculovirus.

The present invention also extends to genetic constructs designed for polypeptide expression. Generally, the genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences. A variety of transcriptional control sequences are well known to those in the art and may be functional in, but are not limited to, a bacterium, yeast, plant, or animal cell. The expression vector can also include a translation regulatory sequence (e.g., an untranslated 5' sequence, an untranslated 3' sequence, a poly A addition site, or an internal ribosome entry site), a splicing sequence or splicing regulatory sequence, and a transcription termination sequence. The vector can be capable of autonomous replication or it can integrate into host DNA.

In an alternative embodiment, the DNA molecule is fused to a reporter gene such as β-glucuronidase gene, chloramphenicol-acetyltransferase gene, a gene encoding green fluorescent protein (and variants thereof), or red fluorescent protein firefly luciferase gene, among others. The DNA molecule can also be fused to a nucleic acid encoding a polypeptideafnity tag, e.g., glutathione S-transferase (GST), maltose E binding protein, or protein A, FLAG tag, hexa-histidine, or the influenza HA tag. The affinity tag or reporter fusion joins the open reading frame of SEQ ID NO: 1 to the reading frame of the reporter gene encoding the affinity tag such that a fusion (hybrid) gene is generated. Expression of the fusion gene results in translation of a single polypeptide that includes both a nematode PGM-like region and reporter protein or affinity tag to create a fusion (hybrid) protein. The fusion can also join a fragment of the reading frame of SEQ ID NO: 1. The fragment can encode a functional region of the PGM-like polypeptides, a structurally-intact domain, or an epitope (e.g., a peptide of about 8, 10, 20, or 30 or more amino acids). A nematode PGM-like nucleic acid that includes at least one of a regulatory region (e.g., a 5' regulatory region, a promoter, an enhancer, a 5' untranslated region, a translational start site, a 3' untranslated region, a polyadenylation site, or a 3' regulatory region) can also be fused to a heterologous nucleic acid. For example, the promoter of a PGM-like nucleic acid can be fused to a heterologous nucleic acid, e.g., a nucleic acid encoding a reporter protein.

Suitable cells to transform include any cell that can be transformed with a nucleic acid molecule of the present invention. A transformed cell of the present invention is also herein referred to as a recombinant cell. Suitable cells can either be untransformed cells or cells that have already been transformed with at least one nucleic acid molecule. Suitable cells for transformation according to the present invention can either be: (i) endogenously capable of expressing the PGM-like protein or; (ii) capable of producing such protein after transformation with at least one nucleic acid molecule of the present invention.

In an exemplary embodiment, a nucleic acid of the invention is used to generate a transgenic nematode stain, e.g., a transgenic *C. elegans* strain. To generate such a strain, nucleic acid is injected into the gonad of a nematode, thus generating a heritable extrachromosomal array containing the nucleic acid (see, e.g., Mello et al. (1991) *EMBO J.* 10:3959–3970). The transgenic nematode can be propagated to generate a strain harboring the transgene. Nematodes of the strain can be used in screens to identify inhibitors specific for a *M. incognita* PGM-like gene.

Oligonucleotides

Also provided are oligonucleotides that can form stable hybrids with a nucleic acid molecule of the present invention. The oligonucleotides can be about 10 to 200 nucleotides, about 15 to 120 nucleotides, or about 17 to 80 nucleotides in length, e.g., about 10, 20, 30, 40, 50, 60, 80, 100, 120 nucleotides in length. The oligonucleotides can be used as probes to identify nucleic acid molecules, primers to produce nucleic acid molecules, or therapeutic reagents to inhibit nematode PGM-like protein activity or production (e.g., antisense, triplex formation, ribozyme, and/or RNA drug-based reagents). The present invention includes oligonucleotides of RNA (ssRNA and dsRNA), DNA, or derivatives of either. The invention extends to the use of such oligonucleotides to protect non-nematode organisms (for example, plants and animals) from disease, e.g., using a technology described herein. Appropriate oligonucleotide-containing therapeutic compositions can be administered to a non-nematode organism using techniques known to those skilled in the art, including, but not limited to, transgenic expression in plants or animals.

Primer sequences can be used to amplify a PGM-like nucleic acid or fragment thereof For example, at least 10 cycles of PCR amplification can be used to obtain such an amplified nucleic acid. Primers can be at least about 8–40, 10–30 or 14–25 nucleotides in length, and can anneal to a nucleic acid "template molecule", e.g. a template molecule encoding a PGM-like genetic sequence, or a functional part thereof, or its complementary sequence. The nucleic acid primer molecule can be any nucleotide sequence of at least 10 nucleotides in length derived from, or contained within sequences depicted in SEQ ID NO: 1, and their complements. The nucleic acid template molecule may be in a recombinant form, in a virus particle, bacteriophage particle, yeast cell, animal cell, plant cell, fungal cell, or bacterial cell. A primer can be chemically synthesized by routine methods.

This invention embodies any PGM-like sequences that are used to identify and isolate similar genes from other organisms, including nematodes, prokaryotic organisms, and other eukaryotic organisms, such as other animals and/or plants.

In another embodiment, the invention provides oligonucleotides that are specific for a *M. incognita* PGM-like nucleic acid molecule. Such oligonucleotides can be used in a PCR test to determine if a*M. incognita* nucleic acid is present in a sample, e.g., to monitor a disease caused by *M. incognita*. Thus, the nucleic acid molecules of the invention can be used diagnostically to detect the presence of *M. incognita*.

Protein Production

Isolated PGM-like proteins from nematodes can be produced in a number of ways, including production and recovery of the recombinant proteins and/or chemical synthesis of the protein. In one embodiment, an isolated nematode PGM-like protein is produced by culturing a cell, e.g., a bacterial, fungal, plant, or animal cell, capable of expressing the protein under conditions for effective production, and recovery of the protein. The nucleic acid can be operably linked to a heterologous promoter, e.g., an inducible promoter or a constitutive promoter. Effective growth conditions are typically, but not necessarily, in liquid media comprising salts, water, carbon, nitrogen, phosphate sources, minerals, and other nutrients, but may be any solution in which PGM-like proteins may be produced.

In one embodiment, recovery of the protein may refer to collecting the growth solution and need not involve additional steps of purification. Proteins of the present invention, however, can be purified using standard purification techniques, such as, but not limited to, affinity chromatography, thermaprecipitation, immunoaffinity chromatography, ammonium sulfate precipitation, ion exchange chromatography, filtration, electrophoresis, hydrophobic interaction chromatography, and others.

The PGM-like polypeptide can be fused to an affinty tag, e.g., a purification handle (e.g., glutathione-S-reductase, hexa-histidine, maltose binding protein, dihydrofolate reductases, or chitin binding protein) or an epitope tag (e.g., c-myc epitope tag, FLAG™ tag, or influenza HA tag). Affinity tagged and epitope tagged proteins can be purified using routine art-known methods.

Antibodies Against PGM-like Polypeptides

Recombinant PGM-like gene products or derivatives thereof can be used to produce immunologically interactive molecules, such as antibodies, or functional derivatives thereof. Useful antibodies include those that bind to a polypeptide that has substantially the same sequence as the amino acid sequences recited in SEQ ID NO: 2, or that has at least 70% similarity over 50 or more amino acids to these sequences. In a preferred embodiment, the antibody specifically binds to a polypeptide having the amino acid sequence recited in SEQ ID NO: 2. The antibodies can be antibody fragments and genetically engineered antibodies, including single chain antibodies or chimeric antibodies that can bind to more than one epitope. Such antibodies may be polyclonal or monoclonal and may be selected from naturally occurring antibodies or may be specifically raised to a recombinant PGM-like protein.

Antibodies can be derived by immunization with a recombinant or purified PGM-like gene or gene product. As used herein, the term "antibody" refers to an immunoglobulin, or fragment thereof Examples of antibody fragments include F(ab) and F(ab')2 fragments, particularly functional ones able to bind epitopes. Such fragments can be generated by proteolytic cleavage, e.g., with pepsin, or by genetic engineering. Antibodies can be polyclonal, monoclonal, or recombinant. In addition, antibodies can be modified to be chimeric, or humanized. Further, an antibody can be coupled to a label or a toxin.

Antibodies can be generated against a full-length PGM-like protein, or a fragment thereof, e.g., an antigenic peptide. Such polypeptides can be coupled to an adjuvant to improve immunogenicity. Polyclonal serum is produced by injection of the antigen into a laboratory animal such as a rabbit and subsequent collection of sera. Alternatively, the antigen is used to immunize mice. Lymphocytic cells are obtained from the mice and fused with myelomas to form hybridomas producing antibodies.

Peptides for generating PGM-like antibodies can be about 8, 10, 15, 20, 30 or more amino acid residues in length, e.g., a peptide of such length obtained from SEQ ID NO: 2. Peptides or epitopes can also be selected from regions exposed on the surface of the protein, e.g., hydrophilic or amphipathic regions. An epitope in the vicinity of the active site can be selected such that an antibody binding such an epitope would block access to the active site. Antibodies reactive with, or specific for, any of these regions, or other regions or domains described herein are provided. An antibody to a PGM-like protein can modulate a PGM-like activity.

Monoclonal antibodies, which can be produced by routine methods, are obtained in abundance and in homogenous form from hybridomas formed from the fusion of immortal cell lines (e.g., myelomas) with lymphocytes immunized with PGM-like polypeptides such as those set forth in SEQ ID NO: 2.

In addition, antibodies can be engineered, e.g., to produce a single chain antibody (see, for example, Colcher et al. (1999) *Ann N Y Acad Sci* 880:263–80; and Reiter (1996) *Clin Cancer Res* 2:245–52). In still another implementation, antibodies are selected or modified based on screening procedures, e.g., by screening antibodies or fragments thereof from a phage display library.

Antibodies of the present invention have a variety of important uses within the scope of this invention. For example, such antibodies can be used: (i) as therapeutic compounds to passively immunize an animal in order to protect the animal from nematodes susceptible to antibody treatment; (ii) as reagents in experimental assays to detect presence of nematodes; (iii) as tools to screen for expression of the gene product in nematodes, animals, fungi, bacteria, and plants; and/or (iv) as a purification tool of PGM-like protein; (v) as PGM inhibitors/activators that can be expressed or introduced into plants or animals for therapeutic purposes.

An antibody against a PGM-like protein can be produced in a plant cell, e.g., in a transgenic plant or in culture (see, e.g., U.S. Pat. No. 6,080,560).

Antibodies that specifically recognize a *M. incognita* PGM-like protein can be used to identify a *M. incognita* nematode, and, thus, can be used to monitor a disease caused by *M. incognita.*

Nucleic Acids Agents

Also featured are isolated nucleic acids that are antisense to nucleic acids encoding nematode PGM-like proteins. An "antisense" nucleic acid includes a sequence that is complementary to the coding strand of a nucleic acid encoding a PGM-like protein. The complementarity can be in a coding region of the coding strand or in a noncoding region, e.g., a 5' or 3' untranslated region, e.g., the translation start site. The antisense nucleic acid can be produced from a cellular promoter (e.g., a RNA polymerase II or III promoter), or can be introduced into a cell, e.g., using a liposome. For example, the antisense nucleic acid can be a synthetic oligonucleotide having a length of about 10, 15, 20, 30, 40, 50, 75, 90, 120 or more nucleotides in length.

An antisense nucleic acid can be synthesized chemically or produced using enzymatic reagents, e.g., a ligase. An antisense nucleic acid can also incorporate modified nucleotides, and artificial backbone structures, e.g., phosphorothioate derivative, and acridine substituted nucleotides.

Ribozymes. The antisense nucleic acid can be a ribozyme. The ribozyme can be designed to specifically cleave RNA, e.g., a PGM-like mRNA. Methods for designing such ribozymes are described in U.S. Pat. No. 5,093,246 or Haselhoff and Gerlach (1988) *Nature* 334:585–591. For example, the ribozyme can be a derivative of Tetrahymena L-19 IVS RNA in which the nucleotide sequence of the active site is modified to be complementary to an PGM-like nucleic acid (see, e.g., Cech et al. U.S. Pat. No. 4,987,071; and Cech et al. U.S. Pat. No. 5,116,742).

Peptide Nucleic acid (PNA). An antisense agent directed against a PGM-like nucleic acid can be a peptide nucleic acid (PNA). See Hyrup et al. (1996) *Bioorganic & Medicinal Chemistry* 4: 5–23) for methods and a description of the replacement of the deoxyribose phosphate backbone for a pseudopeptide backbone. A PNA can specifically hybridize to DNA and RNA under conditions of low ionic strength as a result of its electrostatic properties. The synthesis of PNA oligomers can be performed using standard solid phase peptide synthesis protocols as described in Hyrup et al. (1996) supra; Perry-O'Keefe et a. *Proc. Natl. Acad Sci.* 93: 14670–675.

RNA Mediated Interference (RNAi). A double stranded RNA (dsRNA) molecule can be used to inactivate a PGM-like gene in a cell by a process known as RNA mediated-interference (RNAi; e.g., Fire et al. (1998) *Nature* 391:806–811, and Gönczy et al. (2000) *Nature* 408:331–336). The dsRNA molecule can have the nucleotide sequence of a PGM-like nucleic acid described herein or a fragment thereof. The molecule can be injected into a cell, or a syncitia, e.g., a nematode gonad as described in Fire et al., supra.

Screening Assays

Another embodiment of the present invention is a method of identifying a compound capable of altering (e.g., inhibiting or enhancing) the activity of PGM-like molecules. This method, also referred to as a "screening assay" herein, includes, but is not limited to, the following procedure: (i) contacting an isolated PGM-like protein with a test inhibitory compound, under conditions in which, in the absence of the test compound, the protein has PGM-like activity; and (ii) determining if the test compound alters a PGM-like activity. Suitable inhibitors or activators that alter a nematode PGM-like activity include compounds that interact directly with a nematode PGM-like protein, perhaps but not necessarily, in the active site. They can also interact with other regions of the nematode PGM protein by binding to regions outside of the active site, for example, by allosteric interaction.

Compounds. A test compound can be a large or small molecule, for example, an organic compound with a molecular weight of about 100 to 10,000; 200 to 5,000; 200 to 2000; or 200 to 1,000 daltons. A test compound can be any chemical compound, for example, a small organic molecule, a carbohydrate, a lipid, an amino acid, a polypeptide, a nucleoside, a nucleic acid, or a peptide nucleic acid. Small molecules include, but are not limited to, metabolites, metabolic analogues, peptides, peptidomimetics (e.g., peptoids), amino acids, amino acid analogs, polynucleotides, polynucleotide analogs, nucleotides, nucleotide analogs, organic compounds, or inorganic compounds (i.e., including heteroorganic and organometallic compounds). A metabolite or metabolic analog can be 3-PGA and/or 2-PGA, and derivatives thereof. Compounds and components for synthesis of compounds can be obtained from a commercial chemical supplier, e.g., Sigma-Aldrich Corp. (St. Louis, Mo.). The test compound or compounds can be naturally occurring, synthetic, or both. A test compound can be the only substance assayed by the method described herein. Alternatively, a collection of test compounds can be assayed either consecutively or concurrently by the methods described herein.

Examples of known inhibitors of PGM proteins present in other organisms include clorsulon [MK-401] (Shulman et al. (1982) Mol. and Biochem. Parasit. 5: 321–332 and Martin (1997) The Veterinary Journal. 154: 11–34), vanadate (Fraser (1999) FEBS Letters 455: 344–348), inositol hexakisphosphate, benzene tri-, tetra-, and hexacarboxylates (Rigden (1999) J. Mol. Biol. 289: 691–699). In addition, derivatives and mimetics of 3-PGA and 2-PGA can be screened and/or used.

A high-throughput method can be used to screen large libraries of chemicals. Such libraries of candidate compounds can be generated or purchased, e.g., from Chembridge Corp. (San Diego, Calif.). Libraries can be designed to cover a diverse range of compounds. For example, a library can include 10,000, 50,000, or 100,000 or more unique compounds. Merely by way of illustration, a library can be constructed from heterocycles including pyridines, indoles, quinolines, furans, pyrimidines, triazines, pyrroles, imidazoles, naphthalenes, benzimidazoles, piperidines, pyrazoles, benzoxazoles, pyrrolidines, thiphenes, thiazoles, benzothiazoles, and morpholines. Alternatively, a class or category of compounds can be selected to mimic the chemical structures of 3-PGA, 2-PGA, clorsulon [MK-401], inositol hexakisphosphate, benzene tri-, tetra-, and hexacarboxylates, and vanadate. A library can be designed and synthesized to cover such classes of chemicals, e.g., as described in DeWitt et al. (1993) Proc. Natl. Acad. Sci. U.S.A. 90:6909; Erb et al. (1994) Proc. Natl. Acad. Sci. USA 91:11422; Zuckermannetal. (1994). J. Med. Chem. 37:2678; Cho et al.(1 993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Organism-based Assays. Organisms can be grown in small microtiter plates, e.g., 6-well, 32-well, 64-well, 96-well, 384-well plates.

In one embodiment, the organism is a nematode. The nematodes can be genetically modified. Non-limiting examples of such modified nematodes include: 1) nematodes or nematode cells (e.g., C. elegans or M. incognita) having one or more PGM-like genes inactivated (e.g., using RNA mediated interference); 2) nematodes or nematode cells expressing a heterologous PGM-like gene, e.g., a PGM-like gene from another species; and 3) nematodes or nematode cells having one or more endogenous PGM-like genes inactivated and expressing a heterologous PGM-like gene, e.g., a M. incognita PGM-like gene as described herein.

A plurality of candidate compounds, e.g., a combinatorial library, is screened. The library can be provided in a format that is amenable for robotic manipulation, e.g., in microtitre plates. Compounds can be added to the wells of the microtiter plates. Following compound addition and incubation, viability and/or reproductive properties of the nematodes or nematode cells are monitored.

The compounds can also be pooled, and the pools tested. Positive pools are split for subsequent analysis. Regardless of the method, compounds that decrease the viability or reproductive ability of nematodes, nematode cells, or progeny of the nematodes are considered lead compounds.

In another embodiment, the organism is a microorganism, e.g., a yeast or bacterium. For example, an E. coli strain having deletions or inactivating mutations in E. coli PGM-like genes, but expressing a nematode PGM-like gene can be used. The generation of such strains is routine in the art. As described above for nematodes and nematode cells, the microorganism can be grown in microtitre plates, each well having a different candidate compound or pool of candidate compounds. Growth is monitored during or after the assay to determine if the compound or pool of compounds is a modulator of a nematode PGM-like polypeptide.

In Vitro Activity Assays. The screening assay can be an in vitro activity assay. For example, a nematode PGM-like polypeptide can be purified as described above. The polypeptide can be disposed in an assay container, e.g., a well of microtitre plate. A candidate compound can be added to the assay container, and the PGM-like activity is measured. Optionally, the activity is compared to the activity measured in a control container in which no candidate compound is disposed or in which an inert or non-functional compound is disposed.

A PGM-like activity assay can be an assay for the conversion of 3-PGA to 2-PGA or for the conversion of 2-PGA to 3-PGA.

To measure the conversion of 3-PGA to 2-PGA, the PGM-like polypeptide is disposed in a reaction mixture of 0.1 M triethanolamnine/HCl (pH 7.4), 5.0 mM 3-phosphoglycerate, 1.0 mM $MgSO_4$, 1.0 mM ADP, 0.25 mM NADH, and 0.1% Triton-X 100. Lactate dehydrogenase, enolase, pyruvate are used at final activities of 1 U/ml, 1 U/ml, and 2 U/ml, respectively (Roche).

The activity is monitored by coupling the reaction to lactate dehydrogenase via enolase and pyruvate kinase (Chevalier et al. (2000) Eur. J. Biochem 267: 1464–1472). The reaction is monitored by following the decrease of NADH absorbance at 340 nm, e.g., in a spectrophotometer. A decrease in absorbance at 340 nm is linearly proportional to the amount of NADH expended. The kinetic and equilibrium parameters of the reaction can be determined, e.g., using art-known methods such as Lineweaver-Burk plots and Dixon plots. The assay can be used to measure inhibition coefficients, e.g., a $K_i$, of a candidate compound, by measuring reaction rates at varying concentrations of the candidate compound.

For the conversion of 2-PGA to 3-PGA, the PGM-like polypeptide is disposed in a reaction with 0.1 M triethanolamine/HCl (p.H. 7.4), 5.0 mM 2-phosphoglycerate, 5.0 mM $MgSO_4$, 1.0 mM ATP, 0.42 mM NADH, and 1.0 dithiothreitol. Glyceraldehyde-3-phosphate dehydrogenase and 3-phosphoglycerate kinase are both used at final activities of 4 U/ml (Chevalier et al., supra).

The reaction is monitored by following the decrease in NADH absorbance at 340 nm, e.g., in a spectrophotometer.

In Vitro Binding Assays. The screening assay can also be a cell-free binding assay, e.g., an assay to identify compounds that bind a nematode PGM-like polypeptide. For example, a nematode PGM-like polypeptide can be purified and detectably labeled, e.g., with a fluorescent or radioactive label. The labeled polypeptide is contacted to beads, each bead has a tag detectable by mass spectroscopy, and test compound, e.g., a compound synthesized by combinatorial chemical methods. Beads to which the labeled polypeptide is bound are identified and analyzed by mass spectroscopy. The beads can be generated using "split-and-pool" synthesis. The method can further include a second assay (e.g., the PGM activity assay described above) to determine if the compound alters the activity of the PGM-like polypeptide.

Optimization of a Compound. Once a lead compound has been identified, standard principles of medicinal chemistry can be used to produce derivatives of the compound. Derivatives can be screened for improved pharmacological properties, for example, efficacy, pharnacokinetics, stability, solubility, and clearance. The moieties responsible for a compound's activity in the above-described assays can be delineated by examination of structure-activity relationships (SAR) as is commonly practiced in the art. A person of ordinary skill in chemistry could modify moieties on a lead compound and measure the effects of the modification on the efficacy of the compound to thereby produce derivatives with increased potency. For an example, see Nagarajan et al. (1988) *J. Antibiot.* 41:1430–8. A modification can include N-acylation, amination, amidation, oxidation, reduction, alkylation, esterification, and hydroxylation. Furthermore, if the biochemical target of the lead compound is known or determined, the structure of the target and the lead compound can inform the design and optimization of derivatives. Molecular modeling software is commercially available (e.g., Molecular Simulations, Inc.). "SAR by NMR" as described in Shuker et al. (1996) *Science* 274:1531–4, can be used to design ligands with increased affinity, by joining lower-affinity ligands.

A preferred compound is one that inhibits a PGM-like polypeptide and that is not substantially toxic to plants, animals, or humans. By "not substantially toxic" it is meant that the compound does not substantially affect the respective plant, animal, or human PGM proteins. Thus, particularly desirable inhibitors of *M. incognita* PGM do not substantially inhibit PGM-like polypeptides of cotton, tobacco, pepper, and tomato, for example.

Standard pharmaceutical procedures can be used to assess the toxicity and therapeutic efficacy of a modulator of a PGM-like activity. The LD50 (the dose lethal to 50% of the population) and the ED50 (the dose therapeutically effective in 50% of the population) can be measured in cell cultures, experimental plants (e.g., in laboratory or field studies), or experimental animals. Optionally, a therapeutic index can be determined which is expressed as the ratio: LD50/ED50. High therapeutic indices are indicative of a compound being an effective PGM-like inhibitor, while not causing undue toxicity or side-effects to a subject (e.g., a host plant or host animal).

Alternatively, the ability of a candidate compound to modulate a non-nematode PGM-like polypeptide is assayed, e.g., by a method described herein. For example, the inhibition constant of a candidate compound for a mammalian PGM-like polypeptide or a plant PGM-like polypeptide (e.g., a PGM-like polypeptide from cotton, tobacco, pepper, tomato; Phosphoglycerate Mutase (Tobacco) GenBank Accession No. S44373, GI: 1084422) can be measured and compared to the inhibition constant for a nematode PGM-like polypeptide. (An Advanced Treatise on Meloidogyne, Vol. 1, Sasser and Carter, North Carolina State University Graphics, 1985; Sasser (1980) Plant Disease 64: 36–41)

The aforementioned analyses can be used to identify and/or design a modulator with specificity for nematode PGM-like polypeptide over plant or other animal (e.g., mammalian) PGM-like polypeptides. Suitable nematodes to target are any nematodes with the PGM-like proteins or proteins that can be targeted by a compound that otherwise inhibits, reduces, activates, or generally effects the activity of nematode PGM proteins.

Inhibitors of nematode PGM-like proteins can also be used to identify PGM-like proteins in the nematode or other organisms using procedures known in the art, such as affinity chromatography. For example, a known inhibitor may be linked to a resin and a nematode extract passed over the resin, allowing any PGM-like proteins that bind the inhibitor to bind the resin. Subsequent biochemical techniques familiar to those skilled in the art can be performed to purify and identify bound PGM-like proteins.

Agricultural Compositions

A compound that is identified as a PGM-like polypeptide inhibitor can be formulated as a composition that is applied to plants in order to confer nematode resistance. The composition can be prepared in a solution, e.g., an aqueous solution, at a concentration from about 0.005% to 10%, or about 0.01% to 1%, or about 0.1% to 0.5% by weight. The solution can include an organic solvent, e.g., glycerol or ethanol. The composition can be formulated with one or more agriculturally acceptable carriers. Agricultural carriers can include: clay, talc, bentonite, diatomaceous earth, kaolin, silica, benzene, xylene, toluene, kerosene, N-methylpyrrolidone, alcohols (methanol, ethanol, isopropanol, n-butanol, ethylene glycol, propylene glycol, and the like), and ketones (acetone, methylethyl ketone, cyclohexanone, and the like). The formulation can optionally further include stabilizers, spreading agents, wetting extenders, dispersing agents, sticking agents, disintegrators, and other additives, and can be prepared as a liquid, a water-soluble solid (e.g., tablet, powder or granule), or a paste.

Prior to application, the solution can be combined with another desired composition such another antihelmintic agent, germicide, fertilizer, plant growth regulator and the like. The solution may be applied to the plant tissue, for example, by spraying, e.g., with an atomizer, by drenching, by pasting, or by manual application, e.g., with a sponge. The solution can also be distributed from an airborne source, e.g., an aircraft or other aerial object, e.g., a fixture mounted with an apparatus for spraying the solution, the fixture being of sufficient height to distribute the solution to the desired plant tissues. Alternatively, the composition can be applied to plant tissue from a volatile or airborne source. The source is placed in the vicinity of the plant tissue and the composition is dispersed by diffusion through the atmosphere. The source and the plant tissue to be contacted can be enclosed in an incubator, growth chamber, or greenhouse, or can be in sufficient proximity that they can be outdoors.

If the composition is distributed systemically thorough the plant, the composition can be applied to tissues other than the leaves, e.g., to the stems or roots. Thus, the composition can be distributed by irrigation. The composition can also be injected directly into roots or stems.

A skilled artisan would be able to determine an appropriate dosage for formulation of the active ingredient of the composition. For example, the ED50 can be determined as described above from experimental data. The data can be obtained by experimentally varying the dose of the active ingredient to identify a dosage effective for killing a nematode, while not causing toxicity in the host plant or host animal (i.e. non-nematode animal).

A number of embodiments of the invention have been described. Nevertheless, it will be understood that various modifications may be made without departing from the spirit and scope of the invention. Accordingly, other embodiments are within the scope of the following claims.

What is claimed is:

1. An isolated nucleic acid molecule encoding a polypeptide comprising an amino acid sequence that is at least 95% identical to the amino acid sequence of SEQ ID NO:2, wherein the polypeptide has phosphoglycerate mutase activity.

2. The isolated nucleic acid molecule of claim 1 wherein the amino acid sequence is at least 98% identical to the amino acid sequence of SEQ ID NO:2.

3. An isolated nucleic acid molecule comprising the nucleotide sequence of nucleotides 22 to 1599 of SEQ ID NO: 1.

4. The isolated nucleic acid molecule of claim 1, further comprising a heterologous promoter operably linked to the isolated nucleic acid.

5. An isolated nucleic acid molecule comprising the nucleotide sequence of SEQ ID NO: 1.

6. A vector comprising the isolated nucleic acid molecule of any one of claims 1, 2, 3, 4 and 5.

7. The vector of claim 6 further comprising a heterologous promoter operably linked to the isolated nucleic acid molecule.

8. An isolated host cell comprising the isolated nucleic acid molecule of any one of claims 1, 2, 3, 4 and 5.

9. An isolated host cell comprising the vector of claim 6.

10. An isolated host cell comprising the vector of claim 7.

* * * * *